(12) United States Patent
Shen et al.

(10) Patent No.: US 9,884,313 B2
(45) Date of Patent: Feb. 6, 2018

(54) MIXED METAL IRON OXIDES AND USES THEREOF

(71) Applicant: Research Triangle Institute, Research Triangle Park, NC (US)

(72) Inventors: Jian-ping Shen, Chapel Hill, NC (US); Marty Lail, Raleigh, NC (US); Brian Turk, Durham, NC (US); Paul D. Mobley, Raleigh, NC (US); Jason S. Norman, Chapel Hill, NC (US); Laura Douglas, Durham, NC (US); Jonathan Peters, Durham, NC (US)

(73) Assignee: Research Triangle Institute, Research Triangle Park, NC (US)

( * ) Notice: Subject to any disclaimer, the term of this patent is extended or adjusted under 35 U.S.C. 154(b) by 0 days.

(21) Appl. No.: 14/908,852

(22) PCT Filed: Jul. 31, 2014

(86) PCT No.: PCT/US2014/049007
§ 371 (c)(1),
(2) Date: Jan. 29, 2016

(87) PCT Pub. No.: WO2015/020862
PCT Pub. Date: Feb. 12, 2015

(65) Prior Publication Data
US 2016/0158734 A1 Jun. 9, 2016

Related U.S. Application Data

(60) Provisional application No. 61/860,637, filed on Jul. 31, 2013.

(51) Int. Cl.
| | | |
|---|---|---|
| C07C 29/156 | (2006.01) |
| C07C 2/84 | (2006.01) |
| C07C 5/42 | (2006.01) |
| B01J 23/835 | (2006.01) |
| B01J 23/78 | (2006.01) |
| B01J 23/80 | (2006.01) |
| B01J 23/83 | (2006.01) |
| B01J 23/00 | (2006.01) |
| B01J 23/889 | (2006.01) |
| B01J 23/89 | (2006.01) |
| C10G 27/00 | (2006.01) |
| B01J 23/74 | (2006.01) |

(Continued)

(52) U.S. Cl.
CPC ............ B01J 23/835 (2013.01); B01J 23/002 (2013.01); B01J 23/74 (2013.01); B01J 23/76 (2013.01); B01J 23/78 (2013.01); B01J 23/80 (2013.01); B01J 23/83 (2013.01); B01J 23/8892 (2013.01); B01J 23/8906 (2013.01); B01J 35/002 (2013.01); C01B 3/40 (2013.01); C01B 31/18 (2013.01); C07C 2/84 (2013.01); C07C 5/42 (2013.01); C07C 29/156 (2013.01); C07D 301/03 (2013.01); C10G 27/00 (2013.01); C10J 3/725 (2013.01); B01J 37/03 (2013.01); B01J 37/14 (2013.01); B01J 37/18 (2013.01); B01J 2523/00 (2013.01); C01B 2203/0238 (2013.01); C01B 2203/1047 (2013.01); C01B 2203/1064 (2013.01); C01B 2203/1088 (2013.01); C01B 2203/1235 (2013.01); C07C 2521/04 (2013.01); C07C 2521/06 (2013.01); C07C 2521/08 (2013.01); C07C 2523/46 (2013.01); C07C 2523/74 (2013.01); C07C 2523/78 (2013.01); C07C 2523/80 (2013.01); C07C 2523/83 (2013.01); C07C 2523/835 (2013.01); C07C 2523/889 (2013.01); C07C 2523/89 (2013.01); C07C 2601/16 (2017.05); C10G 2400/22 (2013.01); C10G 2400/30 (2013.01); C10J 2300/0969 (2013.01); C10J 2300/0986 (2013.01); Y02E 20/18 (2013.01); Y02P 20/52 (2015.11)

(58) Field of Classification Search
CPC ... B01J 21/04; B01J 21/06; B01J 21/08; B01J 23/74; B01J 23/78; B01J 23/80; B01J 23/83; B01J 23/835; B01J 23/84; C07C 45/33; C07C 45/34; C07C 45/35; C07C 45/36; C07C 51/252; C07C 51/265; C07C 67/05; C07C 253/24; C07C 253/26; C07C 47/22; C07C 57/04
See application file for complete search history.

(56) References Cited

U.S. PATENT DOCUMENTS

| | | | | |
|---|---|---|---|---|
| 2,728,786 A | * | 12/1955 | McGrath ............... | C07C 1/0445 518/717 |
| 3,424,808 A | * | 1/1969 | Moe ........................ | B01J 23/86 502/313 |

(Continued)

FOREIGN PATENT DOCUMENTS

CN   103084184 A   5/2013

OTHER PUBLICATIONS

Galvita, Vladimir et al., "Ce02-modified Fe203 for C02 utilization via chemical looping"; Industrial and Engineering Chemistry Research, 2013; Mar. 30, 2013; vol. 52, No. 25; pp. 8416-8426.
Acharya, Chethan K. et al., "Tar and C02 removal from stimulated producer gas with activated carbon and charcoal"; Fuel Processing Technology; Feb. 2013; vol. 106; pp. 201-208.
PCT International Search Report and Written Opinion based on PCT/US2014/049007 dated Feb. 27, 2015.
Communication pursuant to Rule 164(1) EPC dated Mar. 7, 2017 from related European Application No. 14833988.0.

(Continued)

Primary Examiner — Jafar Parsa
(74) Attorney, Agent, or Firm — Nathan P. Letts; Olive Law Group, PLLC

(57) ABSTRACT

This invention is directed to novel mixed transition metal iron (II/III) catalysts for the extraction of oxygen from $CO_2$ and the selective reaction with organic compounds.

6 Claims, 25 Drawing Sheets

Figure 1:
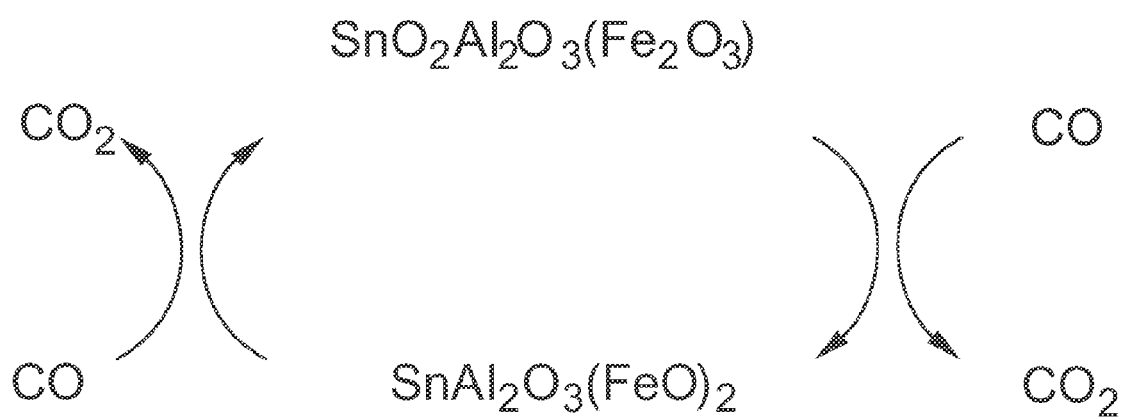

(51) Int. Cl.
*B01J 23/76* (2006.01)
*B01J 35/00* (2006.01)
*C01B 31/18* (2006.01)
*C07D 301/03* (2006.01)
*C10J 3/72* (2006.01)
*C01B 3/40* (2006.01)
*B01J 37/03* (2006.01)
*B01J 37/14* (2006.01)
*B01J 37/18* (2006.01)

(56) References Cited

U.S. PATENT DOCUMENTS

| | | | | |
|---|---|---|---|---|
| 4,058,548 A * | 11/1977 | Olive | ............ | C07C 255/00 |
| | | | | 558/308 |
| 4,066,704 A * | 1/1978 | Harris | ............ | B01J 23/12 |
| | | | | 502/208 |
| 4,143,083 A * | 3/1979 | Riesser | ............ | B01J 23/84 |
| | | | | 502/312 |
| 4,152,300 A * | 5/1979 | Riesser | ............ | B01J 23/84 |
| | | | | 502/302 |
| 4,510,039 A * | 4/1985 | Simone | ............ | B01J 23/745 |
| | | | | 208/423 |
| 4,929,586 A * | 5/1990 | Hegedus | ............ | B01D 53/8628 |
| | | | | 502/217 |
| 4,975,256 A * | 12/1990 | Hegedus | ............ | B01D 53/8628 |
| | | | | 423/239.1 |
| 6,037,295 A * | 3/2000 | Satyavathi | ............ | B01J 21/16 |
| | | | | 502/302 |
| 6,139,723 A * | 10/2000 | Pelrine | ............ | C10G 65/10 |
| | | | | 201/2.5 |
| 6,864,384 B2 * | 3/2005 | Brazdil | ............ | B01J 23/002 |
| | | | | 502/305 |
| 2003/0113244 A1 | 6/2003 | Dupont et al. | | |
| 2008/0031788 A1* | 2/2008 | Brophy | ............ | B01J 19/0093 |
| | | | | 422/207 |
| 2013/0150466 A1 | 6/2013 | Mamedov et al. | | |

OTHER PUBLICATIONS

Lee et al., "Promotion of hydrocarbon selectivity in CO2 hydrogenation by Ru component" Journal of Molecular catalysis A: Chemical 210 (2004) pp. 131-141.

Lima et al., "Ni—Fe catalyst based on perovskite-type oxides for dry reforming of methane to syngas" Catalysis Letter, vol. 108, No. 1-2, pp. 63-70, Apr. 2006.

Maniecki et al. "The Effect of the Nature of the Support on Catalytic Properties of Ruthenium Supported Catalysts in Partial Oxidation of Methane to Syn-Gas" Kenetics and Catalysis, 2011, vol. 52, No. 5, pp. 711-715.

Niemela et al., "Activation of carbon dioxide on Fe-catalysts" Catalysis Today 100 (2005) pp. 269-274.

Australian Examination Report dated Mar. 29, 2017 from related Australian Application No. 2014305050.

* cited by examiner

MIXED METAL IRON OXIDES AND USES THEREOF

CROSS REFERENCE TO RELATED APPLICATIONS

This application is a §371 U.S. National Stage of International Application PCT/US2014/04907, filed Jul. 31, 2014, Shen et al. which claims the benefit of 61/860,637 filed Jul. 31, 2013, Shen et al., which are hereby incorporated by reference in their entireties.

STATEMENT REGARDING FEDERALLY SPONSORED RESEARCH OR DEVELOPMENT

This invention was made with government support under Grant No. DE-FE0004329 awarded by U.S. Department of Energy. The government has certain rights in the invention.

1. FIELD OF THE INVENTION

This invention relates generally to the discovery of novel mixed transition metal iron (II/III) catalysts for the extraction of oxygen from $CO_2$ and the selective reaction with organic compounds.

2. BACKGROUND OF THE INVENTION 2.1. Introduction

The use of $CO_2$ as a chemical feedstock or an oxidant is an appealing strategy for reducing greenhouse gas emissions especially if technologies currently being developed to remove $CO_2$ from fossil fuel fired power plant exhaust gases lead to abundant, high purity, carbon dioxide feedstocks. If the $CO_2$ gas streams can be used as reactants in processes which yield more energetic products, such as fuels or value-added intermediates, then the original carbon in the fossil fuel would be recovered for utilization in another application. Exemplary pathways exist for converting carbon-dioxide to products which can be used in the energy industry for fuel or by the chemical industry for chemical feedstock. These include char gasification to make carbon monoxide from carbon dioxide and carbon, carbon dioxide methanation to make methane from carbon dioxide and hydrogen, and carbon dioxide reforming to make carbon monoxide and hydrogen from carbon dioxide and methane. See, for example Kolb and Kolb, 1983, J Chem Ed 60(1) 57-59 "Organic Chemicals from Carbon Dioxide." Others have reported on studies of $CO_2$ as a reagent for organic synthesis. See Colmenares, 2010, Current Organic Synthesis 7(6) 533-542 "Novel Trends in the Utilization of $CO_2$ as a Reagent and Mild Oxidant in the C—C Coupling Reactions." The potential for the upgrading of carbon dioxide through industrial processes has been investigated for over the past one hundred years.

Specifically, U.S. Pat. No. 4,185,083, Walker, discloses a process using the Boudouard Reaction to produce finely divided carbon. U.S. Pat. No. 4,496,370, Billings, and U.S. Pat. No. 4,382,915, Sadhukhan and Billings, disclose a zinc oxide-char gasification process. U.S. Pat. No. 7,259,286, Jothimurugesan et al. disclose iron oxide catalysts for carbon monoxide hydrogenation reactions such as Fischer-Tropsch reaction. The contents of the above are hereby incorporated in its entirety.

Towards these uses certain iron-based materials have been reported due to the high reactivity of reduced iron for oxidation. For example, Tada et al. disclose Fe-valve metal-Pt group elements (including Ru) alloys activated by hydrofluoric acid (HF) for the conversion of $CO_2$ and $H_2$ to methane (methanation of $CO_2$). Tada, et al., AMORPHOUS FE-VALVE METAL-PT GROUP METAL ALLOY CATALYSTS FOR METHANATION OF $CO_2$. Mater. Sci. Eng. A-Struct. Mater. Prop. Microstruct. Process. 1994, 182, 1133-1136.

Recently, Coker et al. reported iron oxide supported on zirconia or yttria-stabilized zirconia (YSZ) for the solar thermal production of hydrogen from water or CO from $CO_2$. Coker et al. J. Mat. Chem 2012 22 6726-6732.

3. SUMMARY OF THE INVENTION

In particular non-limiting embodiments, the present invention provides a mixed transition metal iron (II/III) catalyst for catalyzing $CO_2$ oxidation of carbon or an organic compound. In one embodiment, the mixed transition metal iron (II/III) catalyst is an iron (II/III) and a transition metal selected from the group consisting of Ag, Bi, Co, Cu, La, Mn, Sn, Sr, Ru, and Zn. The mixed transition metal iron (II/III) catalyst may further comprise a support and/or an alkali or alkaline-earth element promoter. The support may be $Al_2O_3$, $SiO_2$, $TiO_2$, $ZrO_2$ or a mixture thereof.

The mixed transition metal iron (II/III) catalyst may have the formula $Fe_2O_3(SnO_2)_{0.1-10}(Al_2O_3)_{0.1-10}$ or the formula $Fe_2O_3(SnO_2)_{1.0-3.0}(Al_2O_3)_{1.0-3.0}$.

Alternatively, the mixed transition metal iron (II/III) catalyst may have the formula $(RuO_2)_{0.001-0.2}Fe_2O_3$, or $(RuO_2)_{0.005-0.05}Fe_2O_3$.

The invention also provides a method for converting $CO_2$ and carbon to carbon monoxide which comprises contacting the mixed transition metal iron (II/III) catalyst with an appropriate $CO_2$ feed stream under appropriate conditions. The mixed transition metal iron (II/III) catalyst, and the appropriate $CO_2$ feed stream may be reacted together at the same time in a suitable reactor such as a fluidized bed.

In another embodiment, the invention provides a method for converting a hydrocarbon to an oxygenated hydrocarbon which comprises contacting the mixed transition iron (II/III) metal catalyst with the hydrocarbon and an appropriate $CO_2$ feed stream under appropriate conditions so as to form the oxygenated hydrocarbon. In some embodiments the catalyst may be combined with reactants which are fed simultaneously to a reaction zone. In other embodiments the catalyst itself may be transported between reaction zones containing separate reactant feed streams.

The hydrocarbon may be an alkane, an alkene, an alkyne, an aromatic compound, a cyclic compound, a polyaromatic compound or a polycyclic compound. The oxygenated hydrocarbon may be an alcohol, aldehyde, an anhydride, a carboxylic acid, an ester, an ether, an epoxide, or a ketone. In one embodiment, the epoxide is ethylene oxide or propylene oxide.

The invention also provides a method for oxidative dehydrogenation (ODH) of a first hydrocarbon comprises contacting the mixed transition iron (II/III) metal catalyst with the first hydrocarbon and an appropriate $CO_2$ feed stream under appropriate conditions so as to form a dehydrogenated second hydrocarbon. The first hydrocarbon may be an alkane, an alkene, an alkyne, an aromatic compound, a cyclic compound, a polyaromatic compound or a polycyclic compound. For this method, the first hydrocarbon is methane and the second hydrocarbon is ethane or a higher molecular weight hydrocarbon. For this method the first hydrocarbon can be methane or any other saturated hydrocarbon and the second hydrocarbon product contains carbon atoms in which there are fewer carbon-hydrogen bonds when compared to the first hydrocarbon.

In the methods above, the alkane may be butane, ethane, methane, or propane; the alkene may be ethylene or propylene; aromatic compound may be ethyl benzene; or the cyclic compound may be cyclohexane.

4. BRIEF DESCRIPTION OF THE FIGURES

FIG. 1. Removal of oxygen from carbon dioxide by a reduced iron catalyst.

Figure 2:
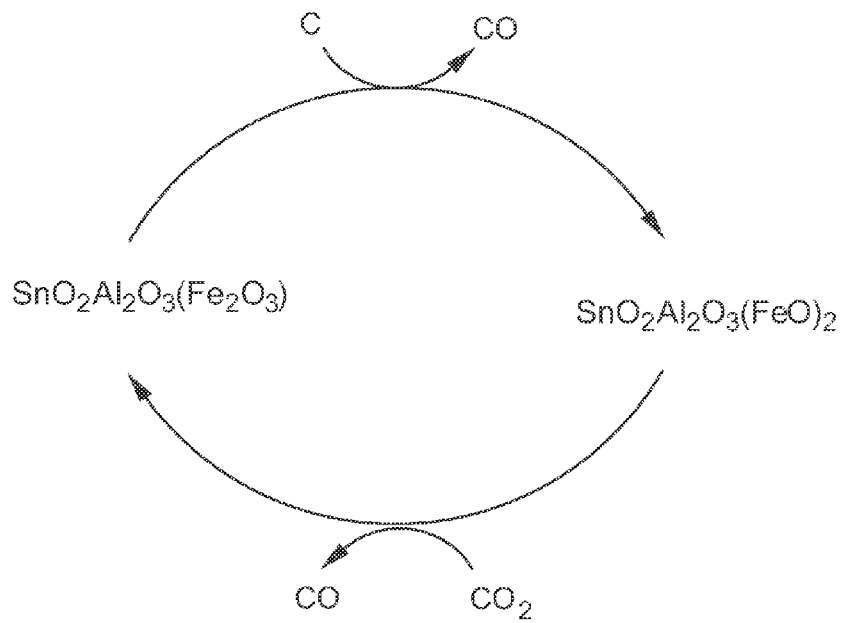
Figure 2:
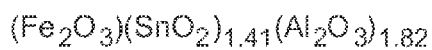

FIG. 2. Oxidation and reduction scheme in thermogravimetric experiments and nominal catalyst formulation.

Figure 3:
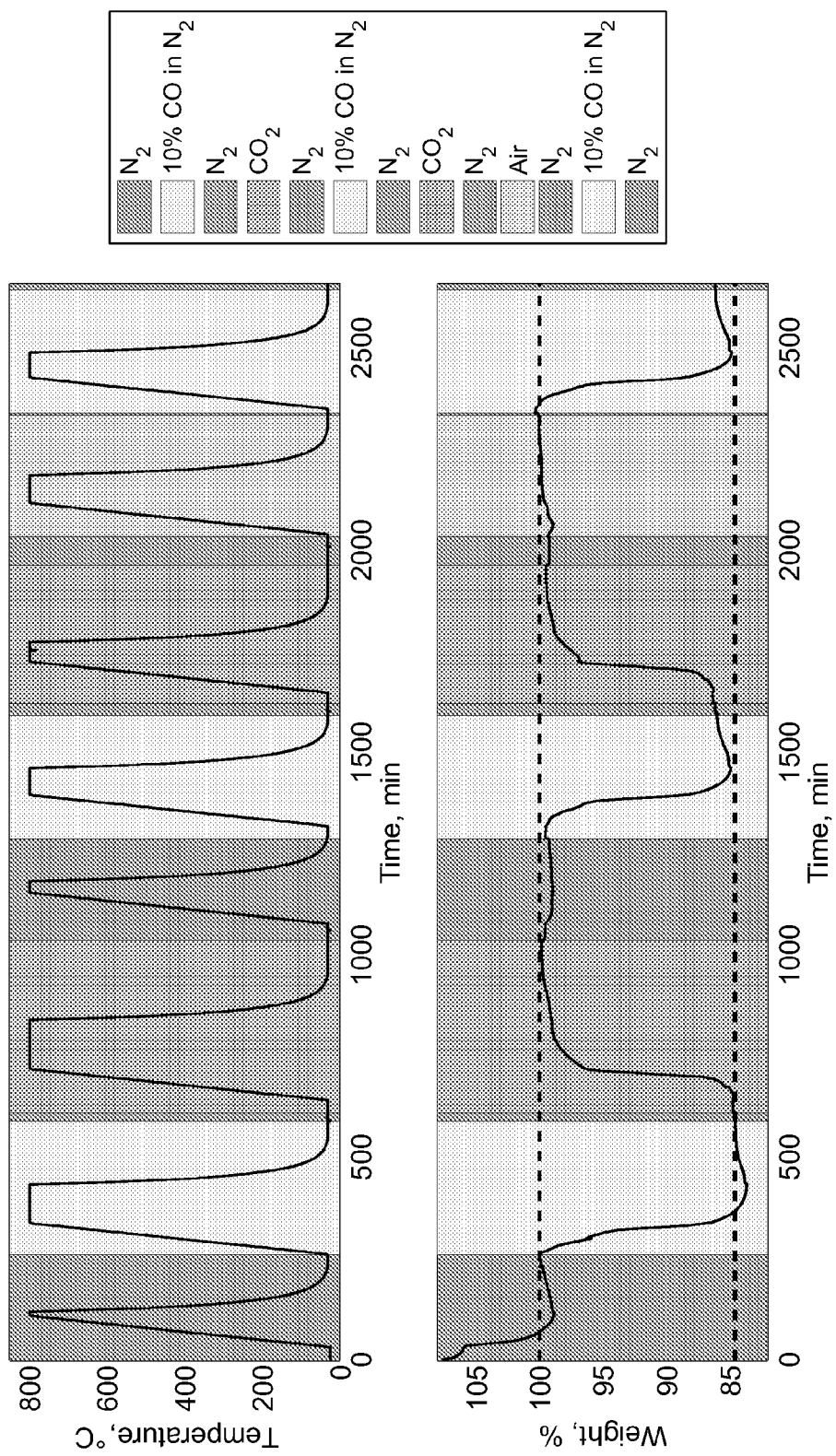

FIG. 3. Percent weight change of catalyst during thermo gravimetric analysis (bottom) and the corresponding temperature (top) in run 1.

Figure 4:
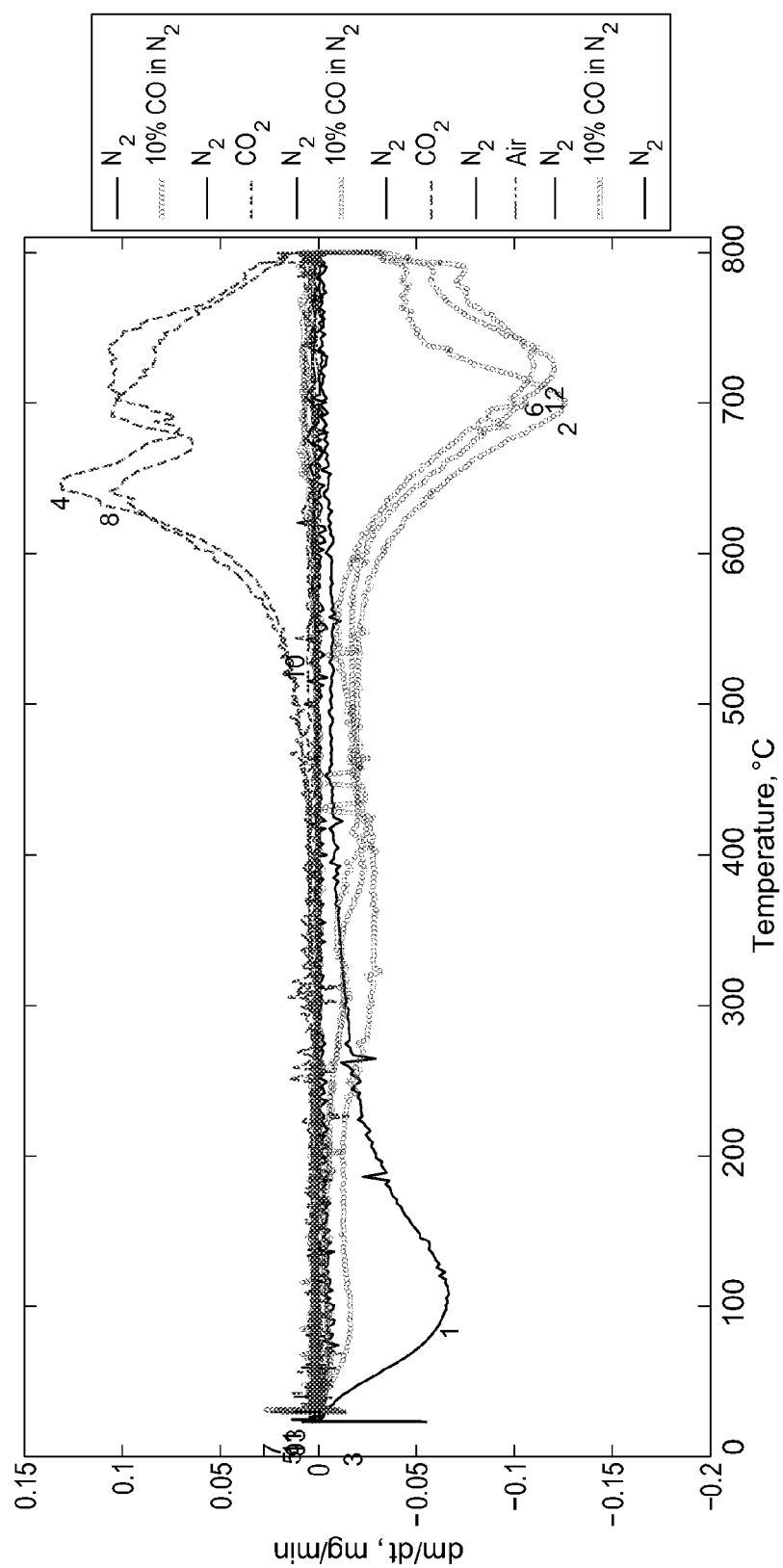

FIG. 4. Rate of weight change of catalyst versus temperature in run 1. The numbers denote the order of each step in the method to the left of its extreme.

Figure 5:
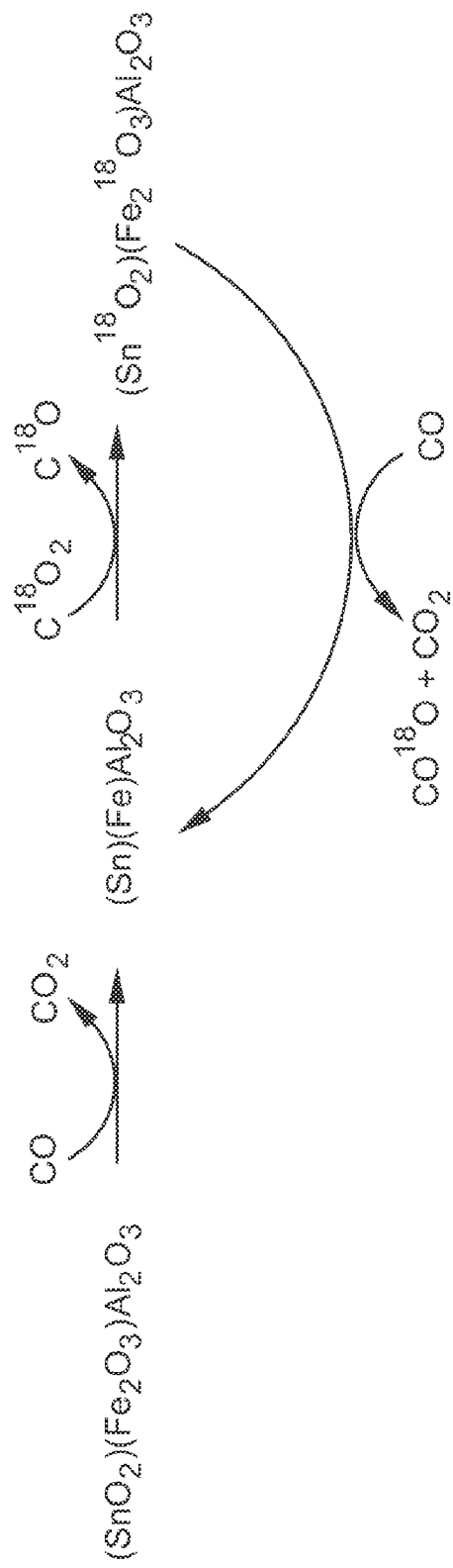

FIG. 5. Labeling of $(SnO_2)(Fe_2O_3)Al_2O_3$ catalyst using $C^{18}O_2$.

Figure 6:
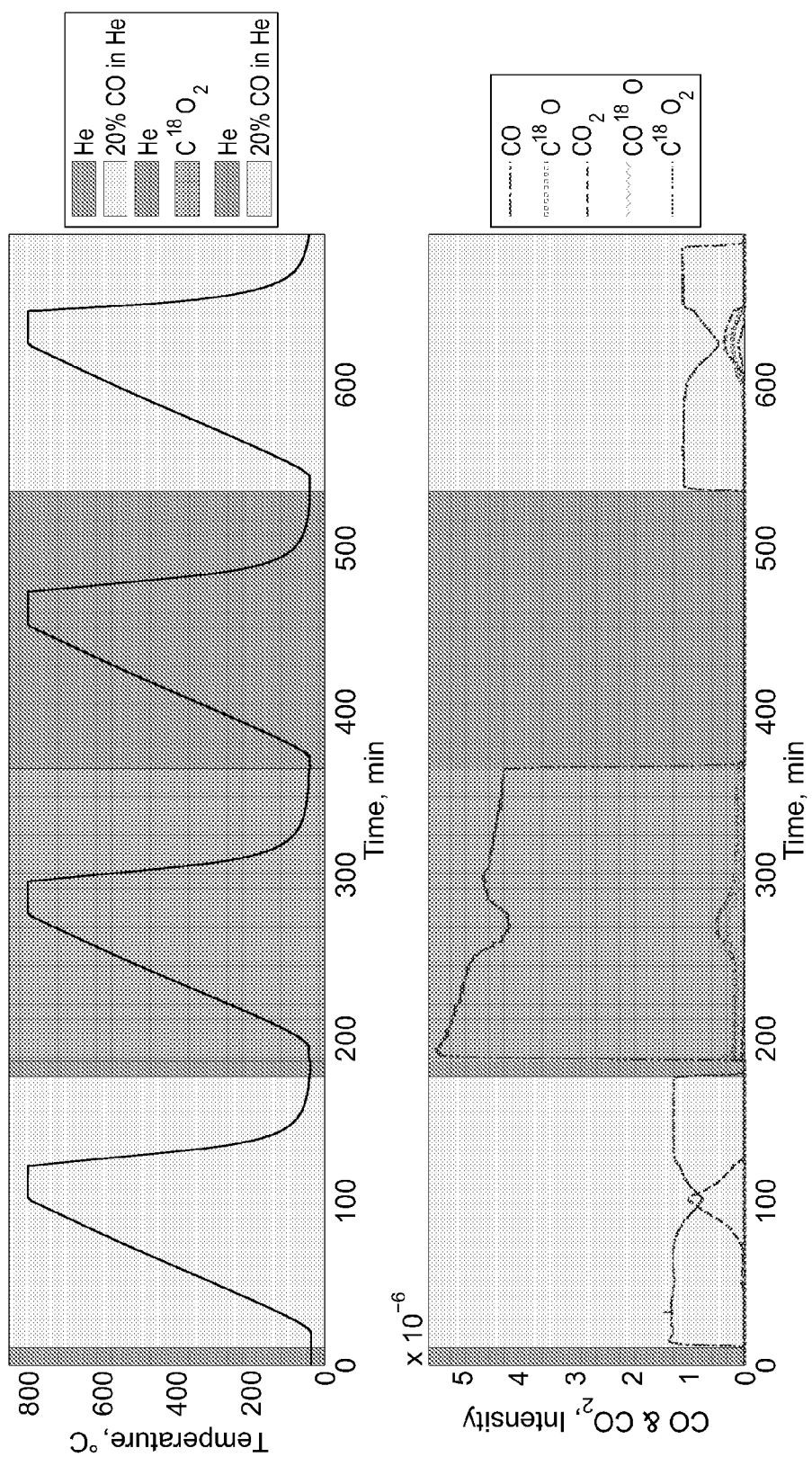

FIG. 6. Mass spectrometry signals of relevant species over time (below), and the corresponding temperature (above).

Figure 7:
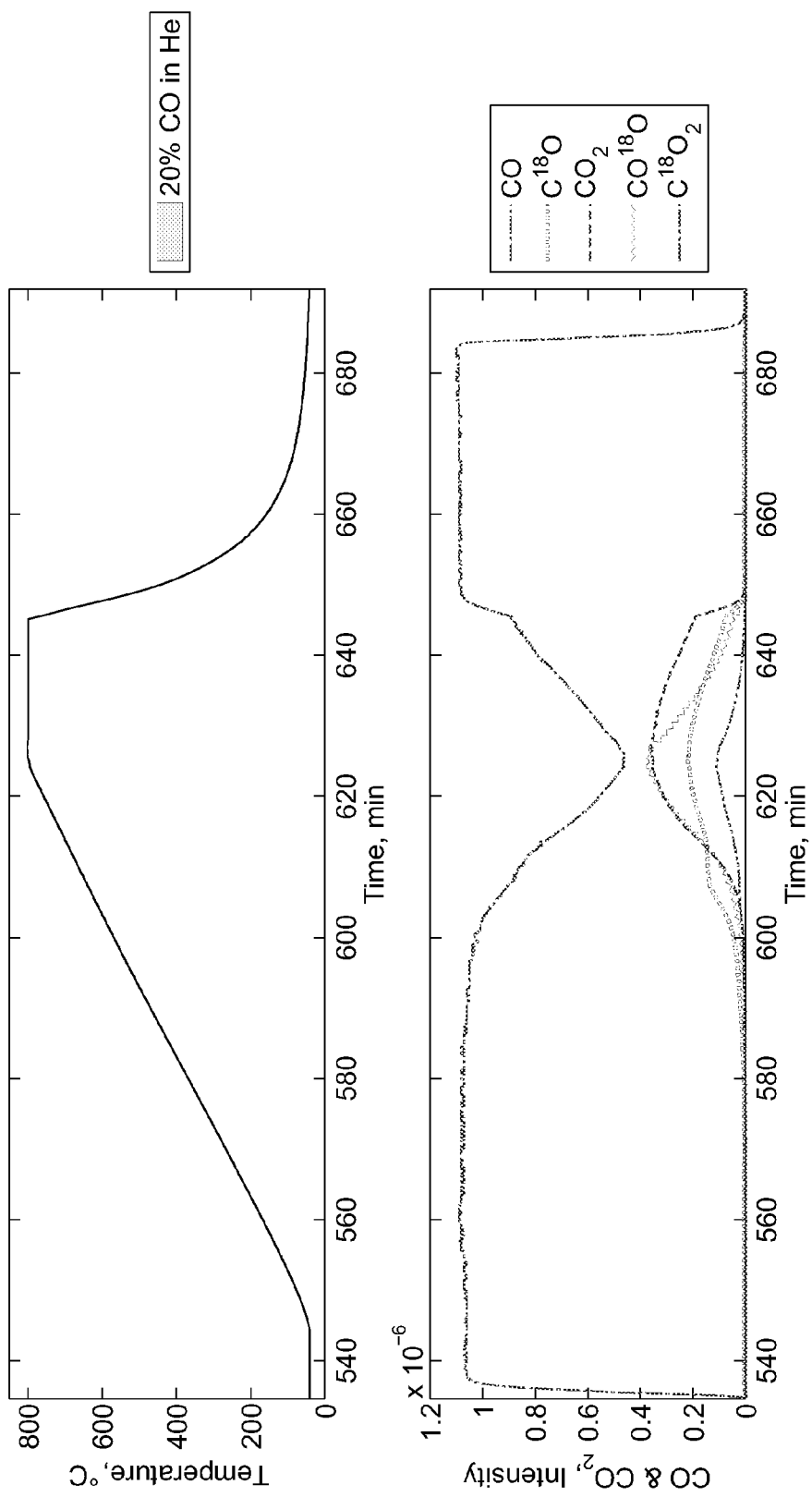

FIG. 7. Mass spectrometry signals of relevant species during Step 4 (below) and the corresponding temperature (above).

Figure 8:
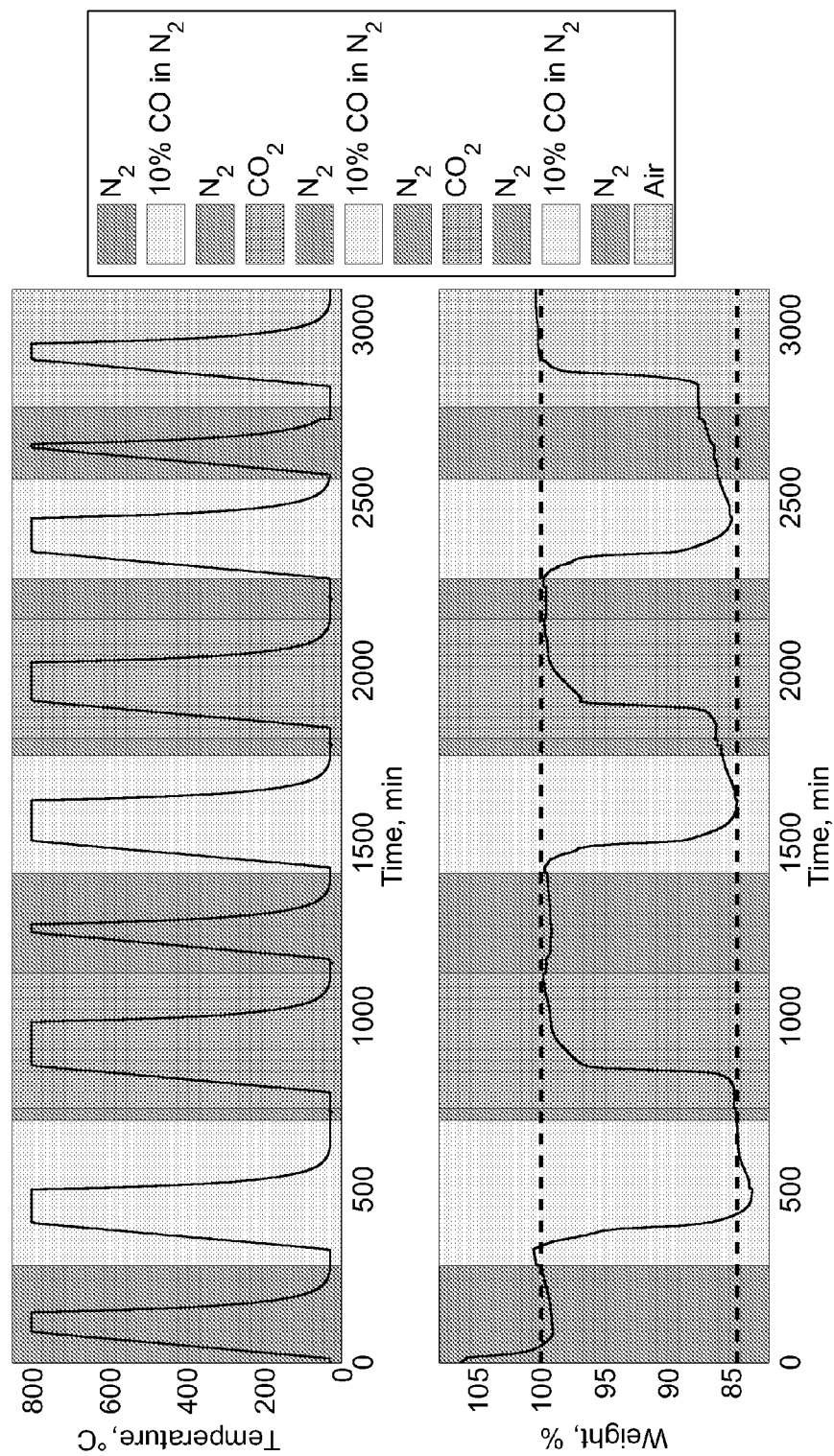

FIG. 8: Percent weight change of catalyst during thermogravimetric analysis (bottom), and the corresponding temperature (top) in run 2.

Figure 9:
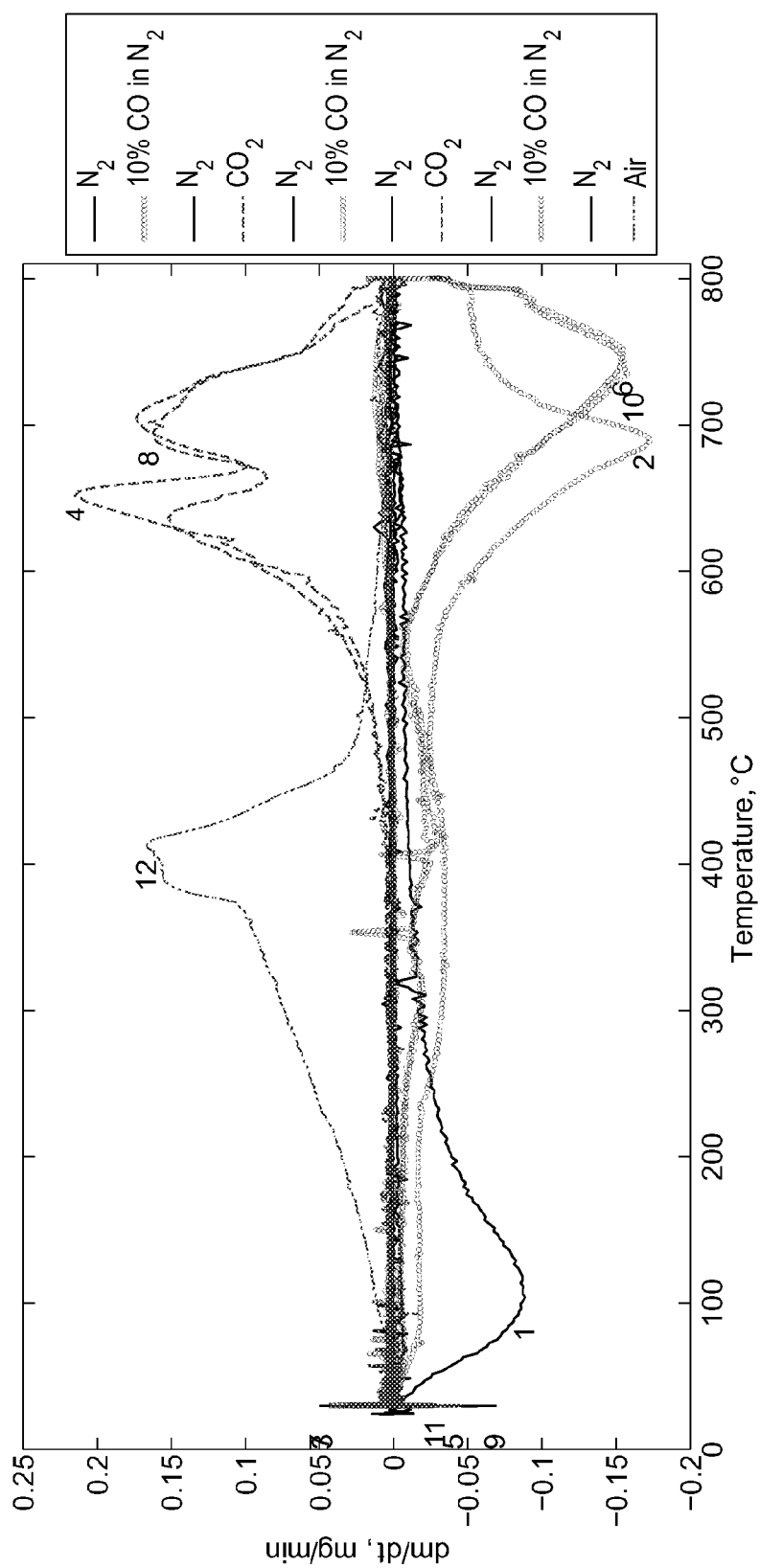

FIG. 9: Rate of weight change of catalyst versus temperature in run 2. The numbers denote the order of each step in the method to the left of its extreme.

Figure 10:
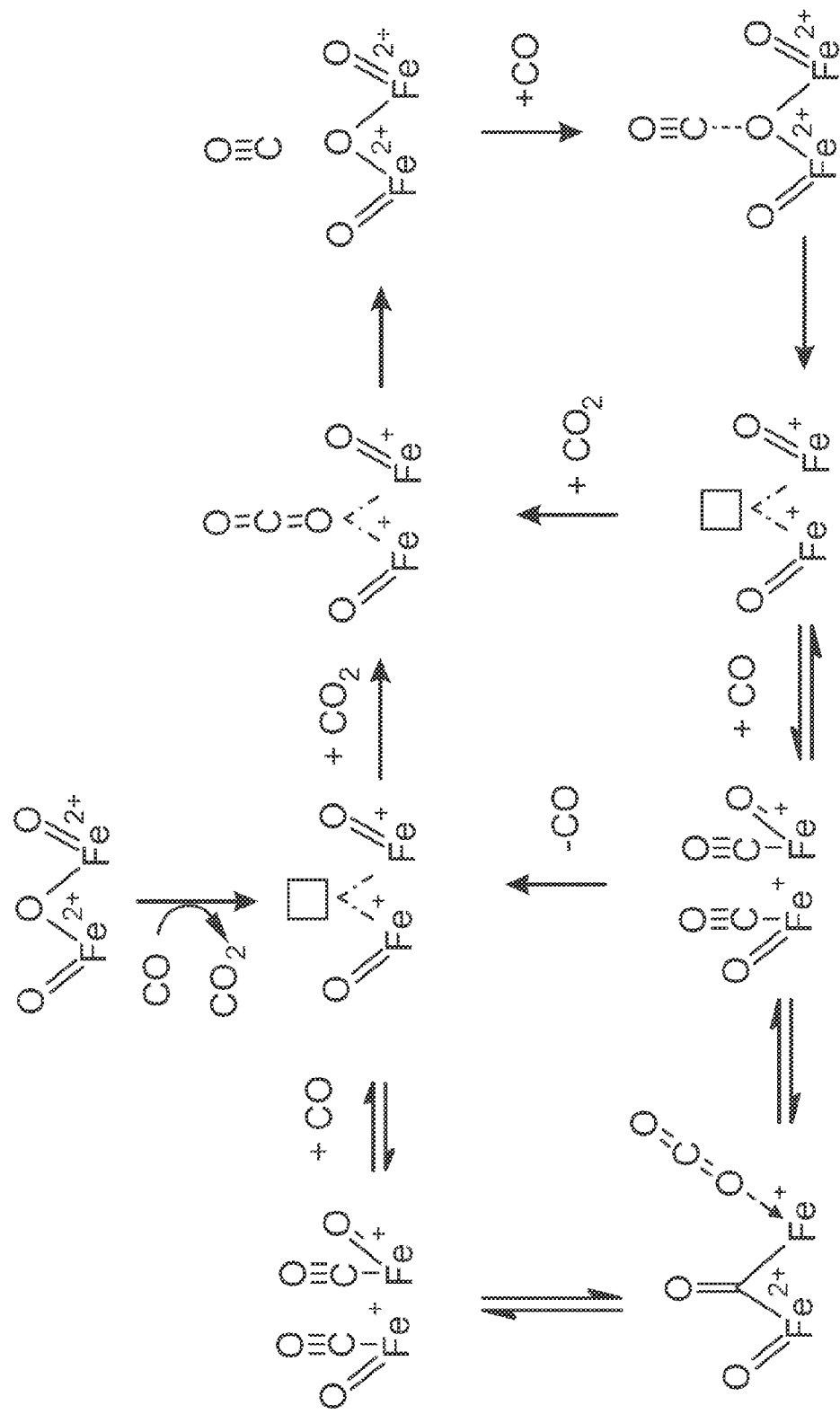

FIG. 10: Proposed mechanism for metal-mediated $CO_2$ utilization via conversion to CO.

Figure 11:
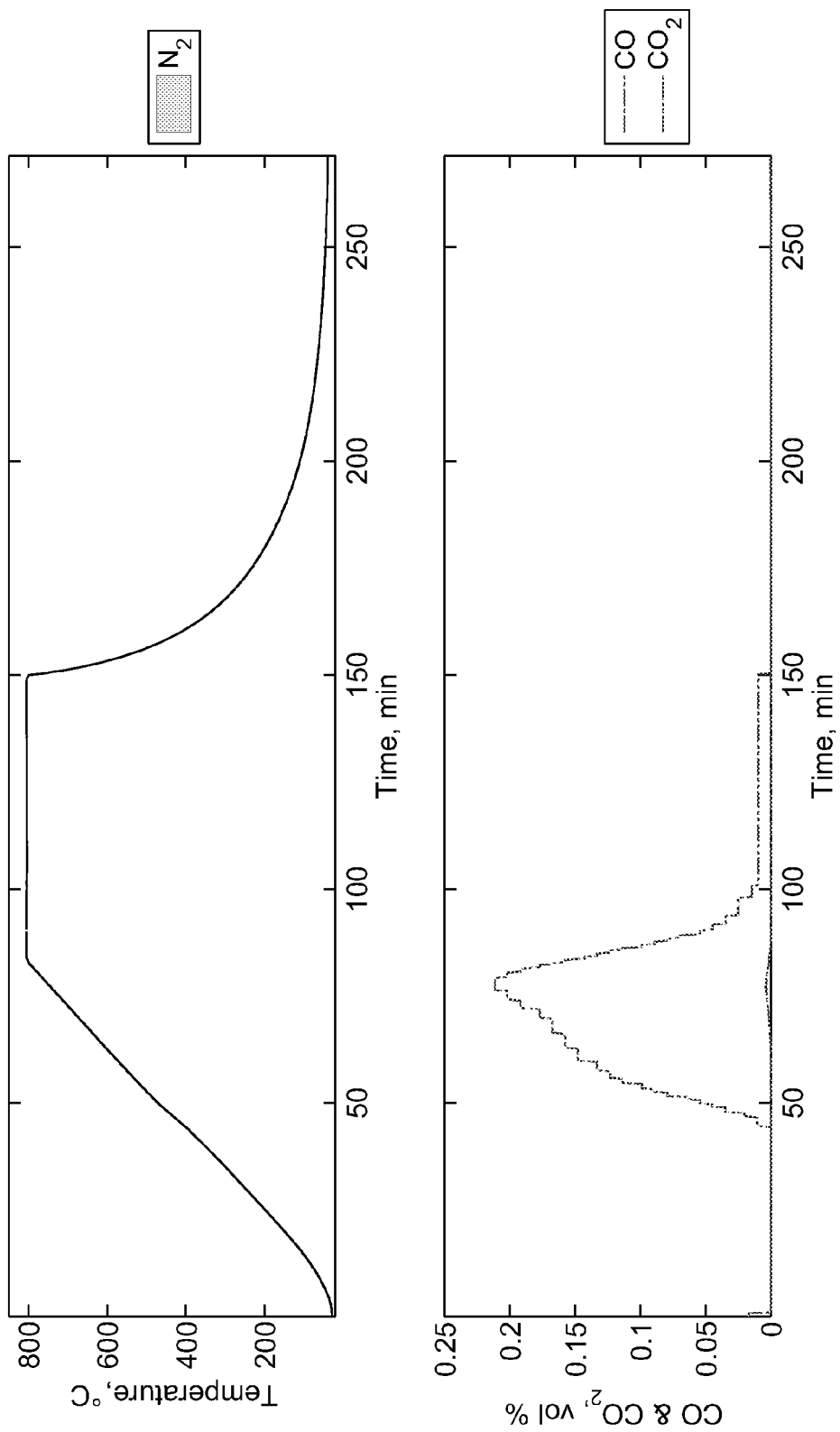

FIG. 11: Temperature, CO, and $CO_2$ profiles as a function of time—Step 1

Figure 12:
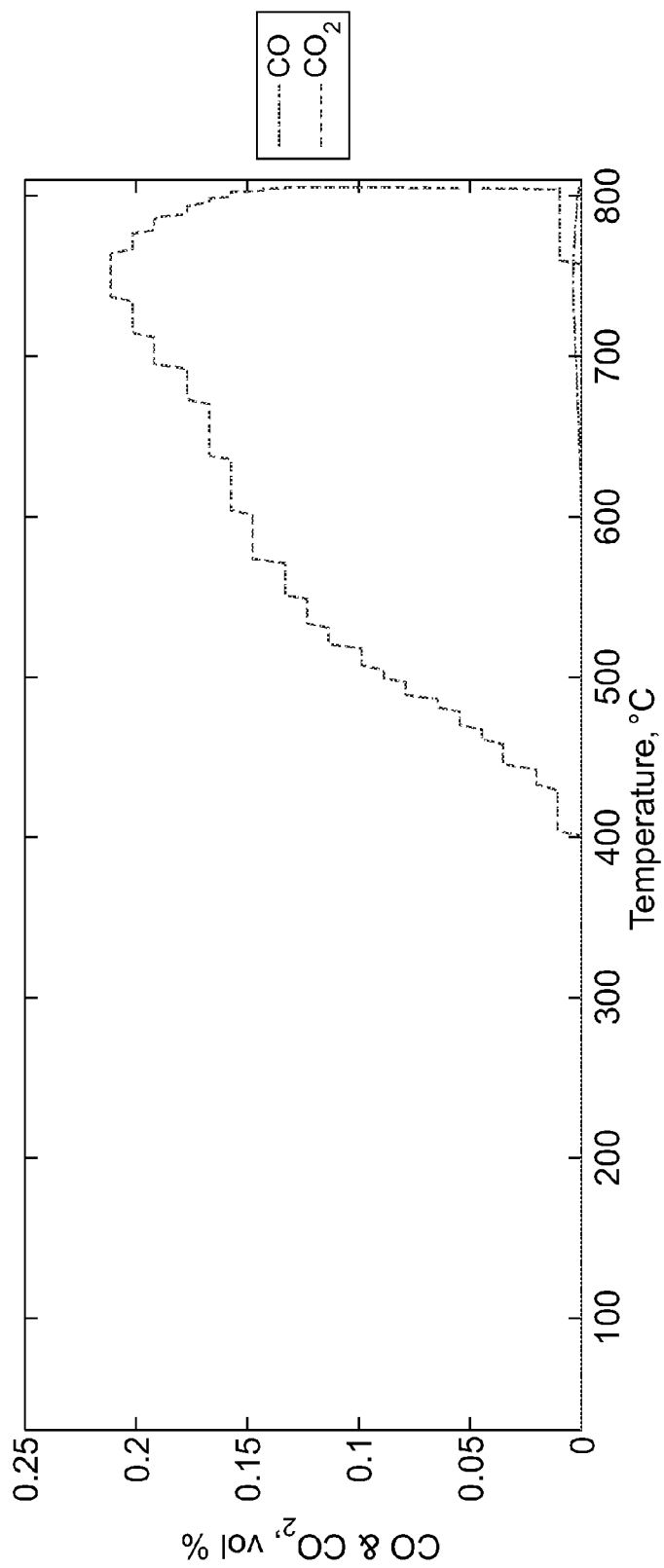

FIG. 12: CO and $CO_2$ profiles as a function of temperature—Step 1

Figure 13:
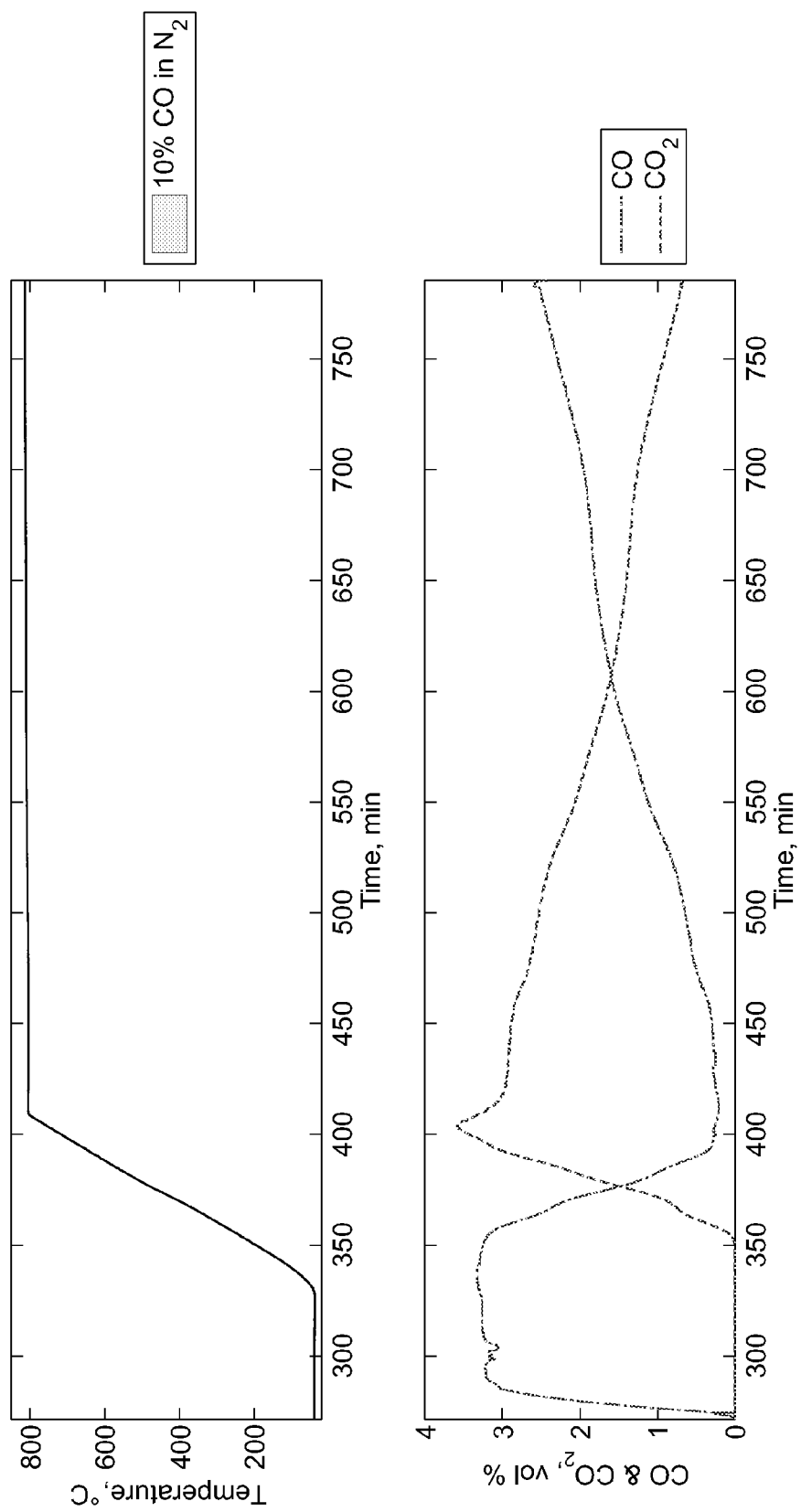

FIG. 13: Temperature, CO, and $CO_2$ profiles as a function of time—Step 2

Figure 14:
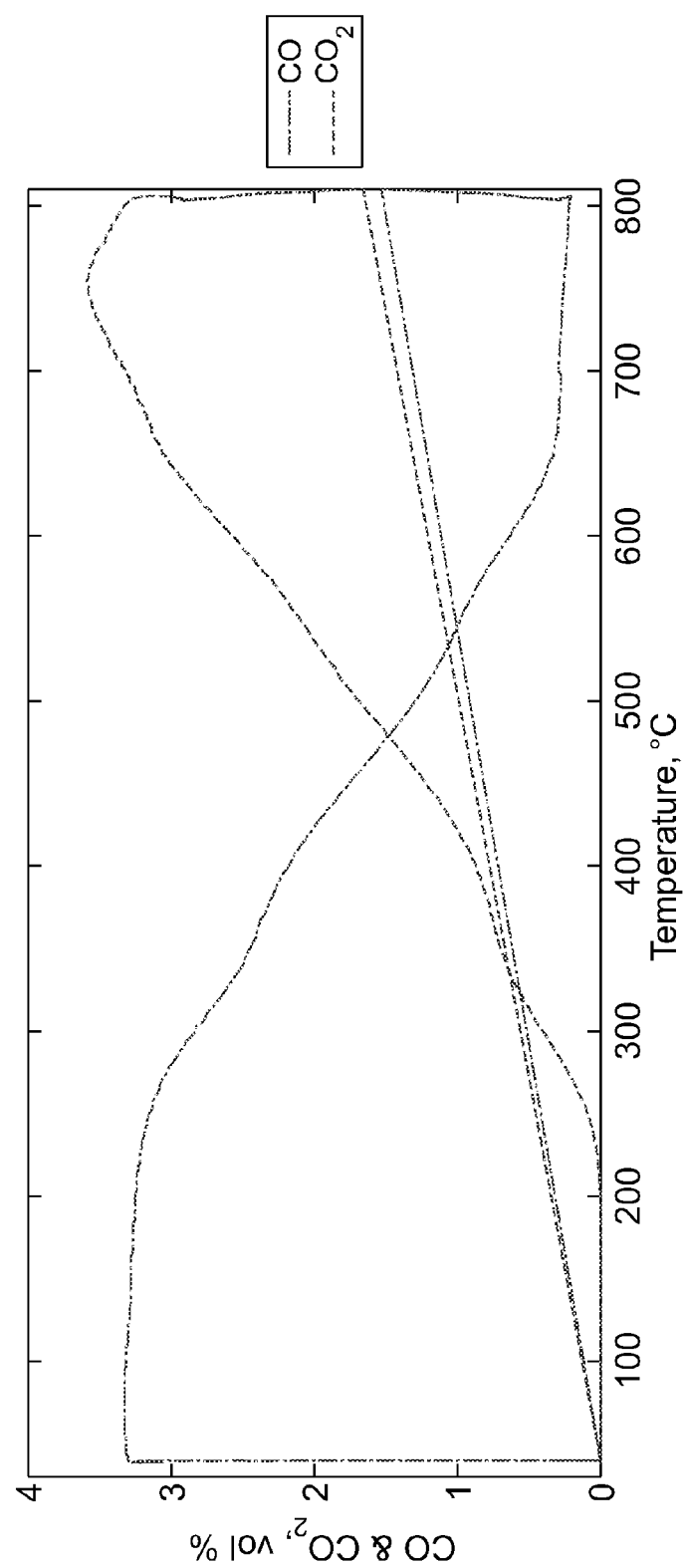

FIG. 14: CO and $CO_2$ profiles as a function of temperature—Step 2

Figure 15:
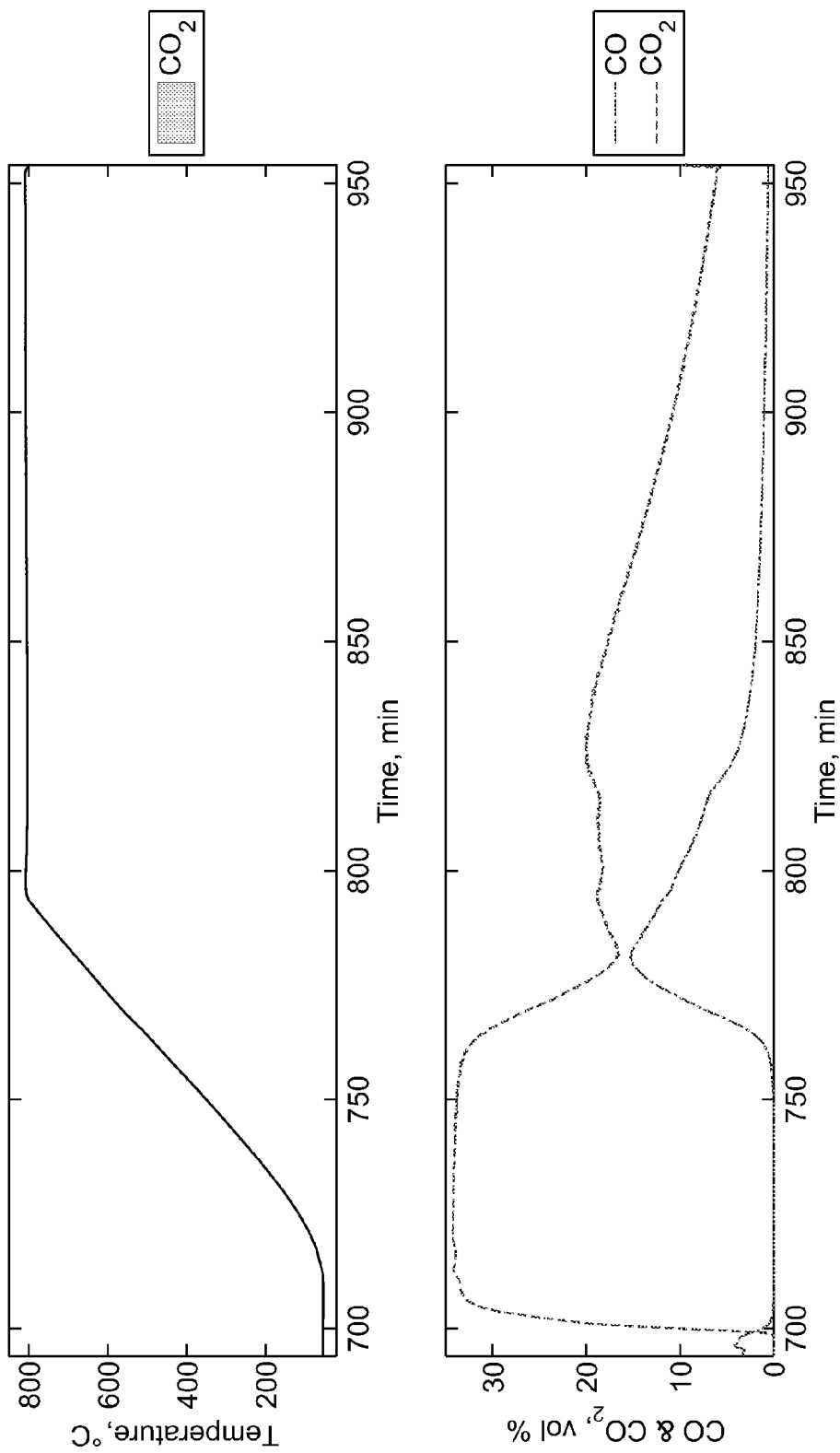

FIG. 15: Temperature, CO, and $CO_2$ profiles as a function of time—Step 3

Figure 16:
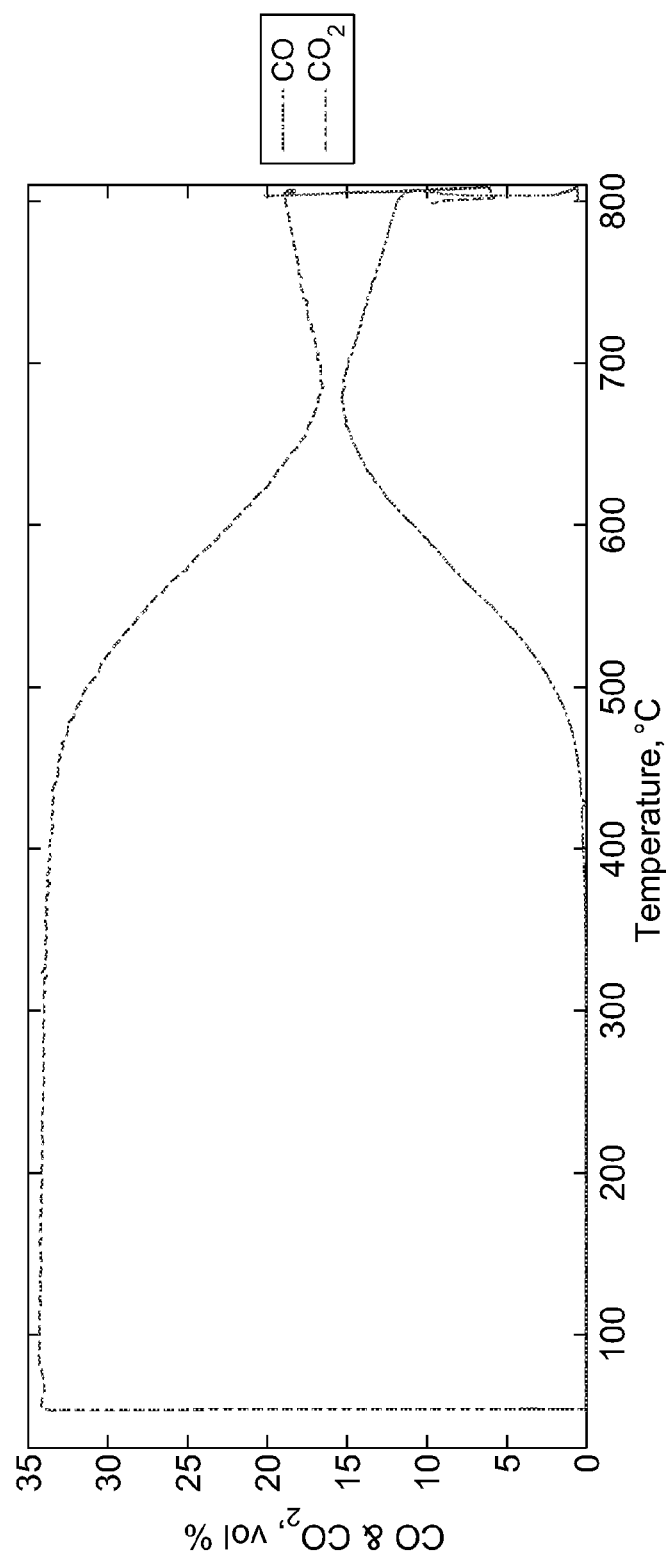

FIG. 16: CO and $CO_2$ profiles as a function of temperature—Step 3

Figure 17:
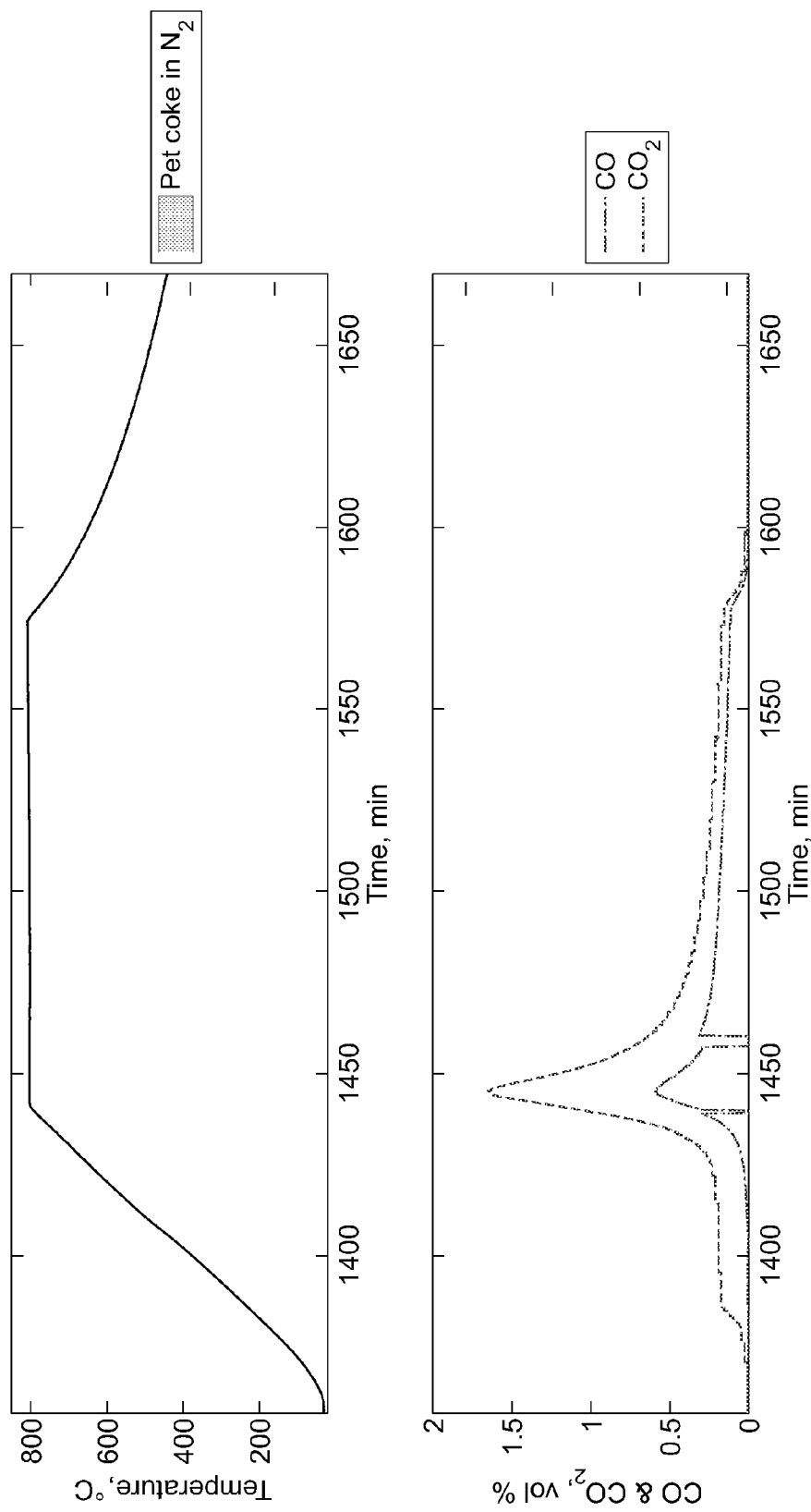

FIG. 17: Temperature, CO, and $CO_2$ profiles as a function of time—Step 4

Figure 18:
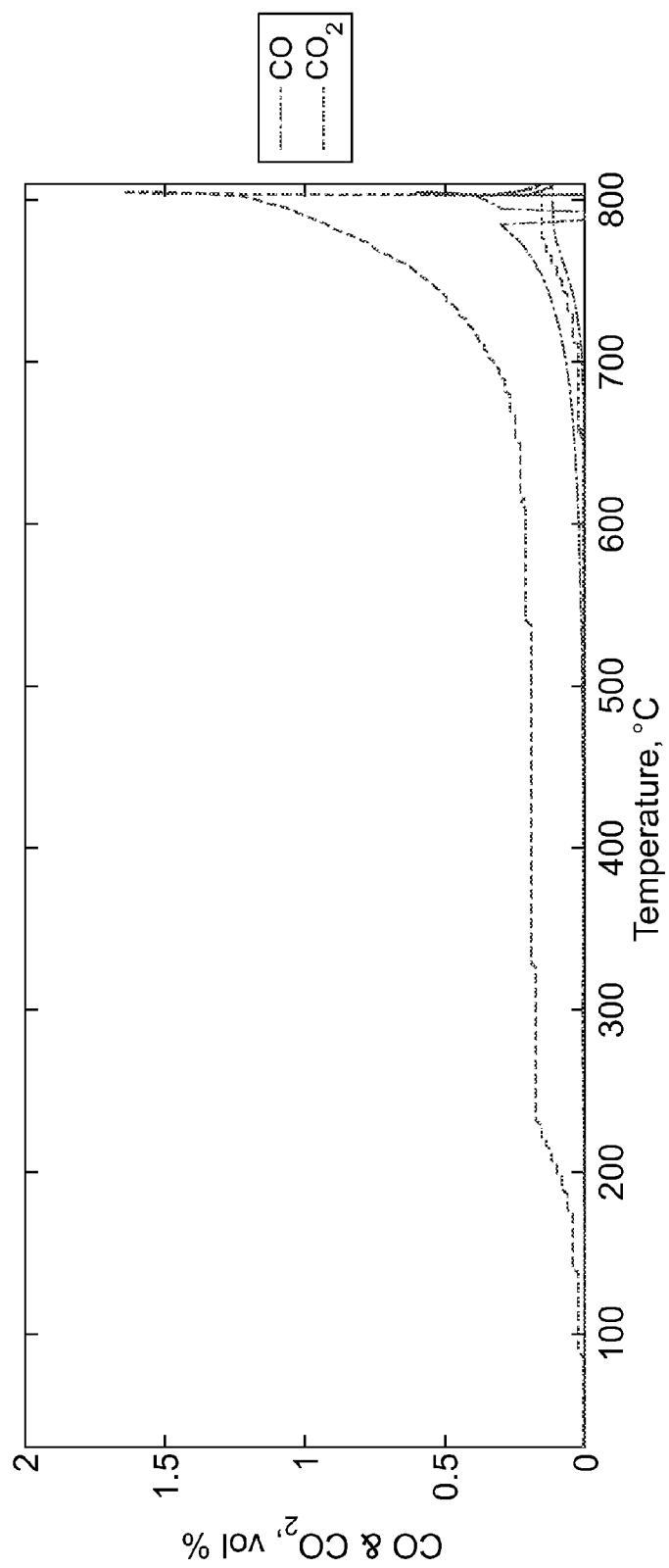

FIG. 18: CO and $CO_2$ profiles as a function of temperature—Step 4

Figure 19:
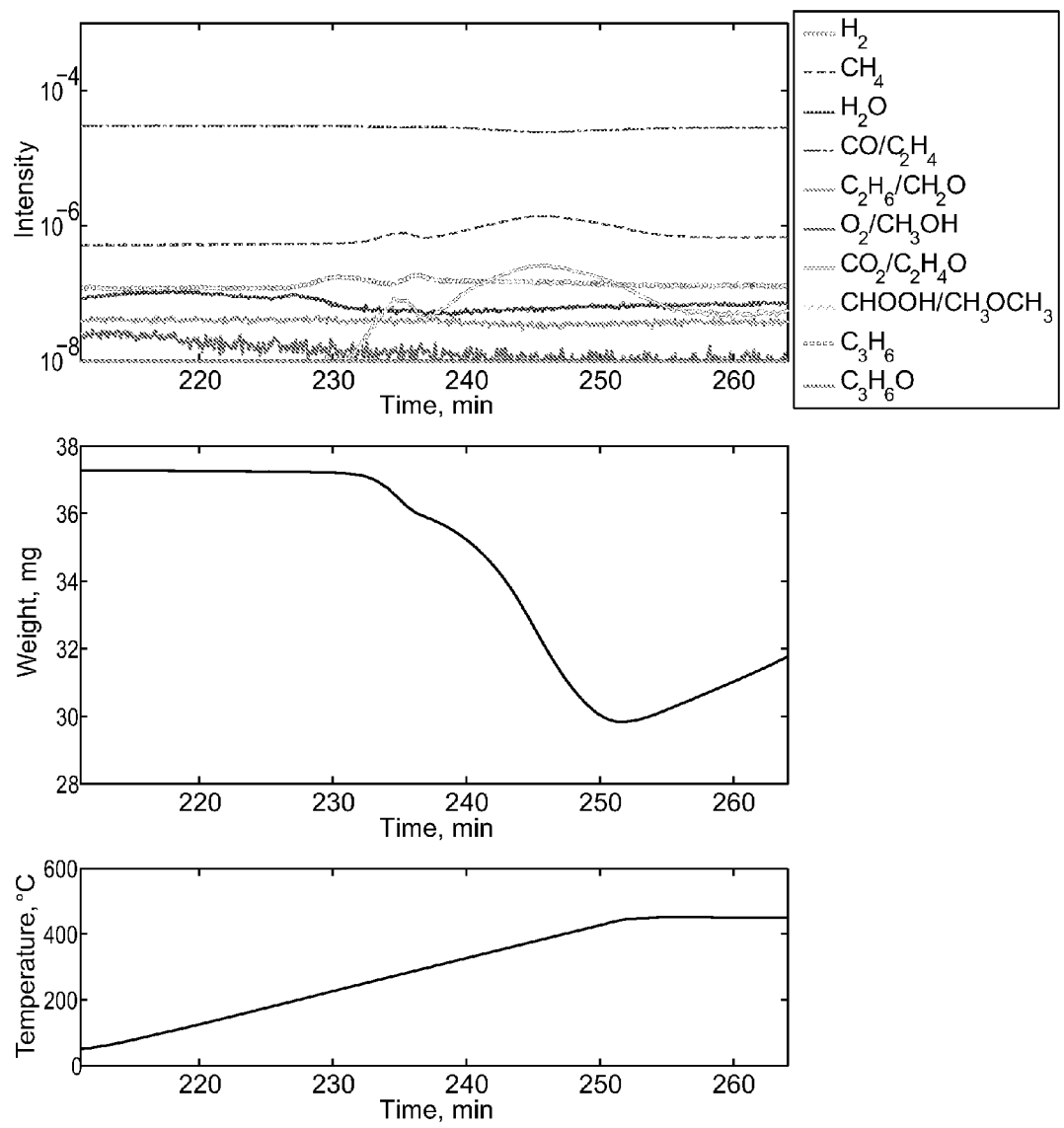

FIG. 19. Reduction of $(RuO)_{0.1}(Fe_2O_3)$ with 0.2 atm CO.

Figure 20:
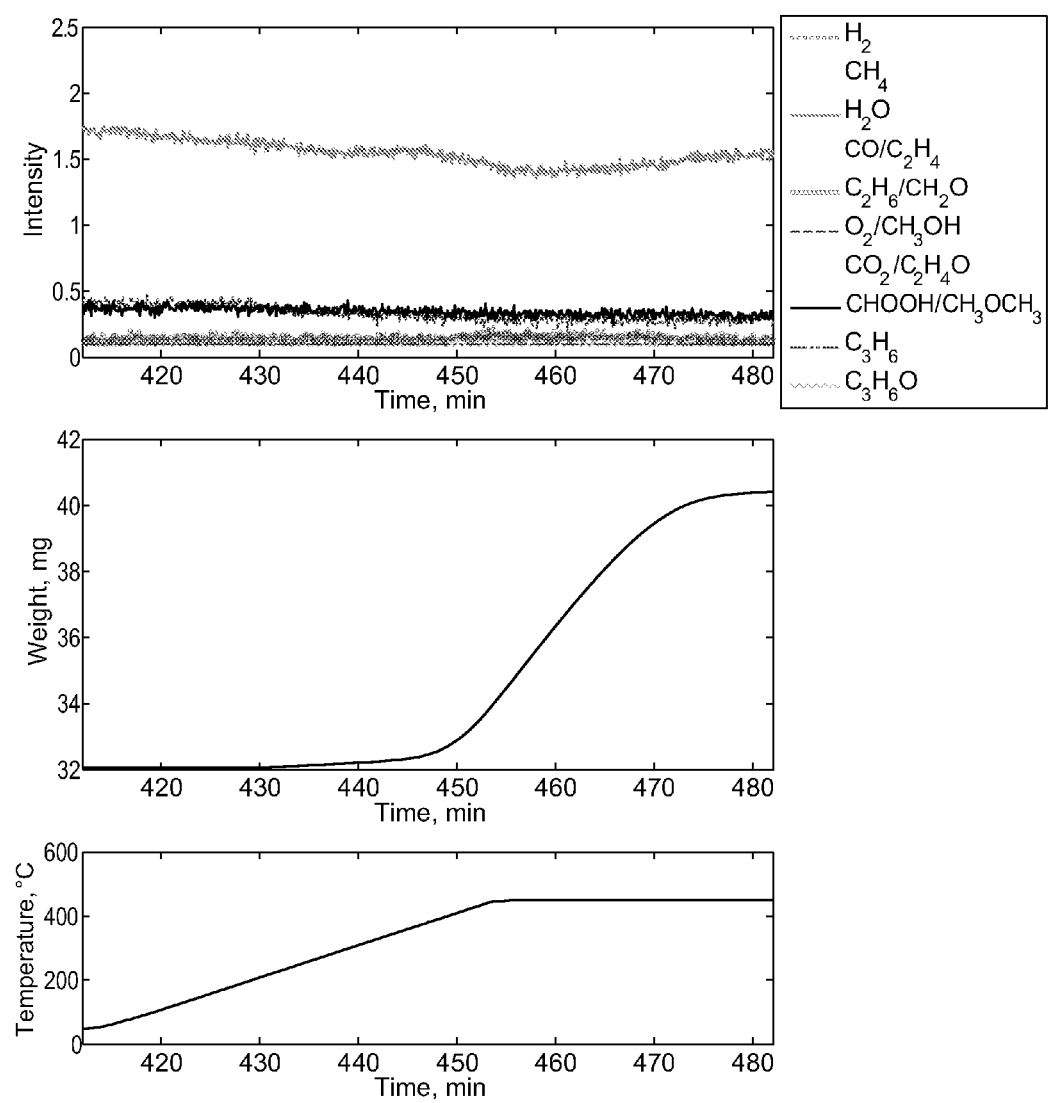

FIG. 20. Oxidation of $(RuO)_{0.1}(Fe_2O_3)$ with 1 atm $CO_2$.

Figure 21:
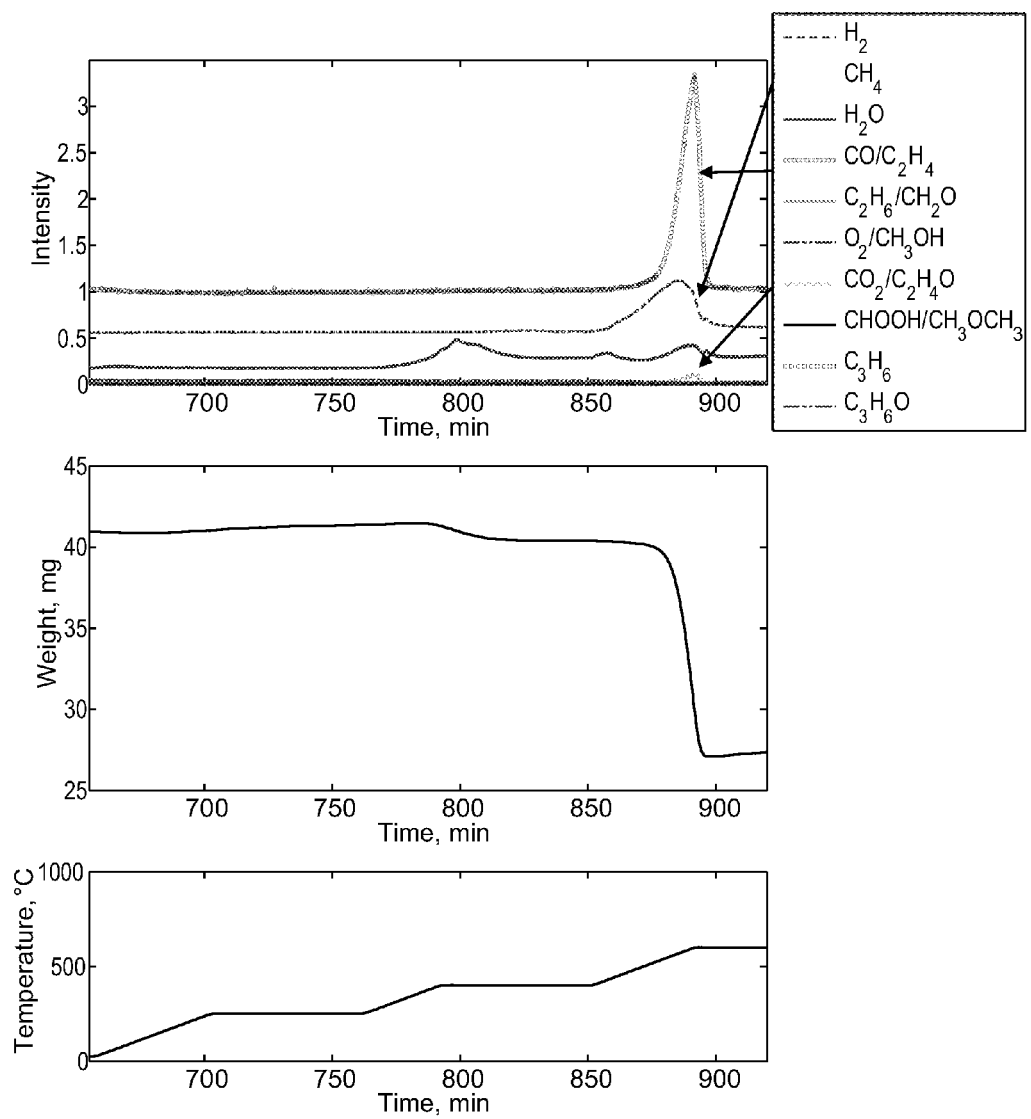

FIG. 21. Reduction of $(RuO)_{0.1}(Fe_2O_3)$ with 1 atm $CH_4$.

Figure 22:
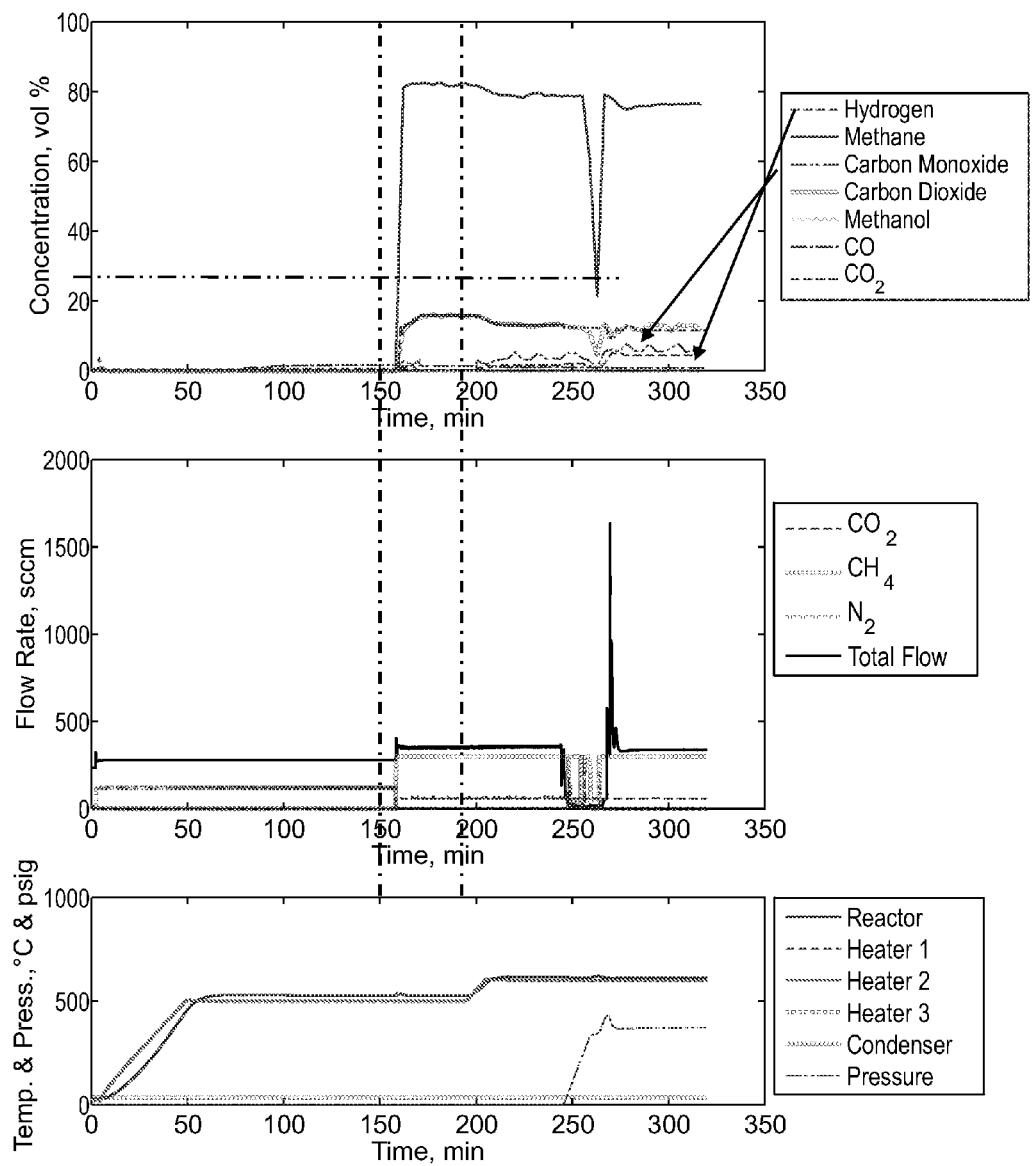

FIG. 22. At 500° C. (6:1 $CH_4$:$CO_2$, 1 bar), there is little CO or $H_2$ detected. When the temperature is increased to 600° C., CO and $H_2$ are detected. When the pressure is raised to 25 bar, about 10 vol % CO and $H_2$ is detected.

Figure 23:
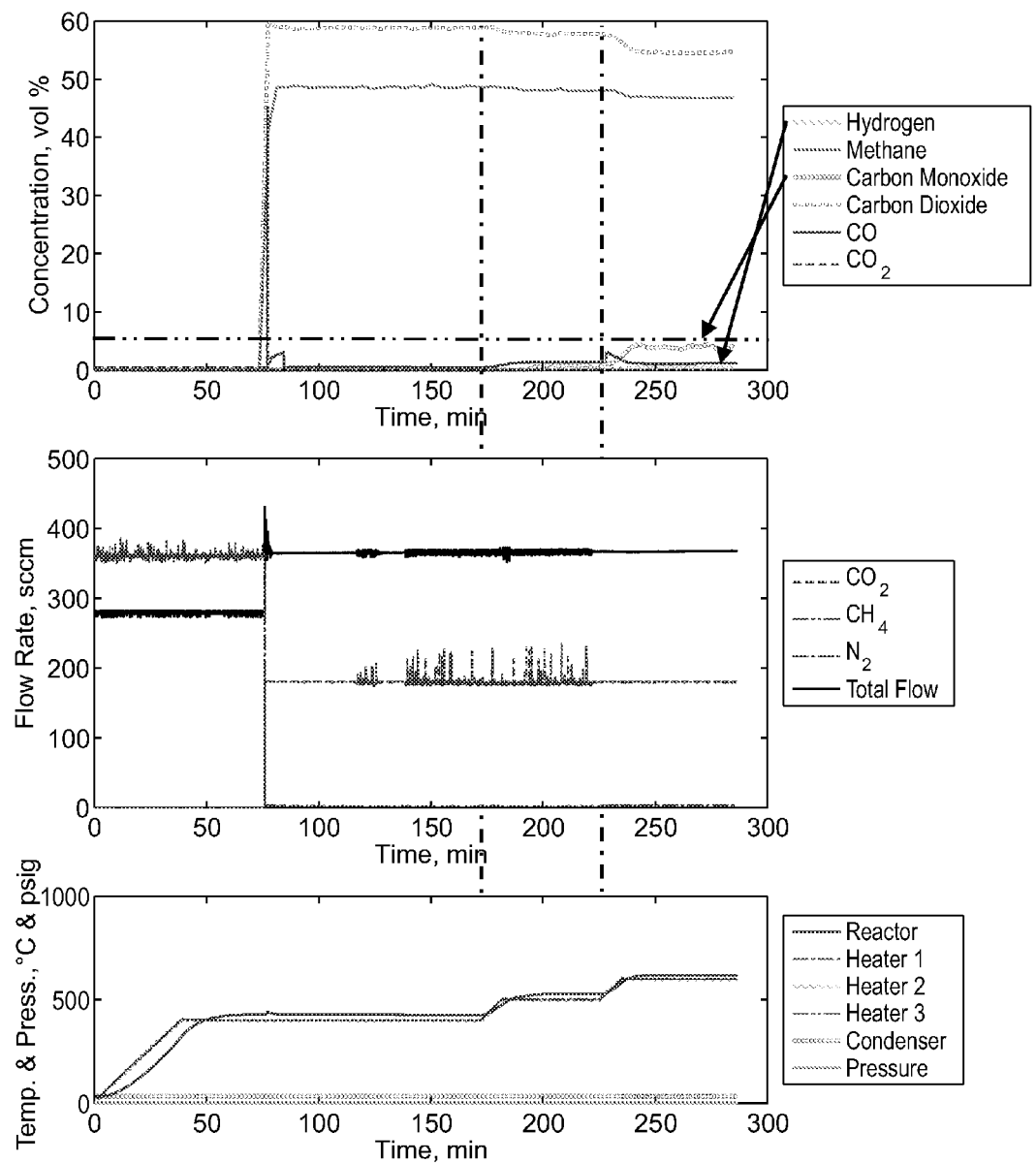

FIG. 23. At 1 bar (1:1 $CO_2$:$CH_4$) at 400° C. there is little synthesis gas products. At 500° C. there is approximately 2.5 vol % CO detected and at 600° C. there is approximately 5 vol % CO and 1 vol % $H_2$.

Figure 24:
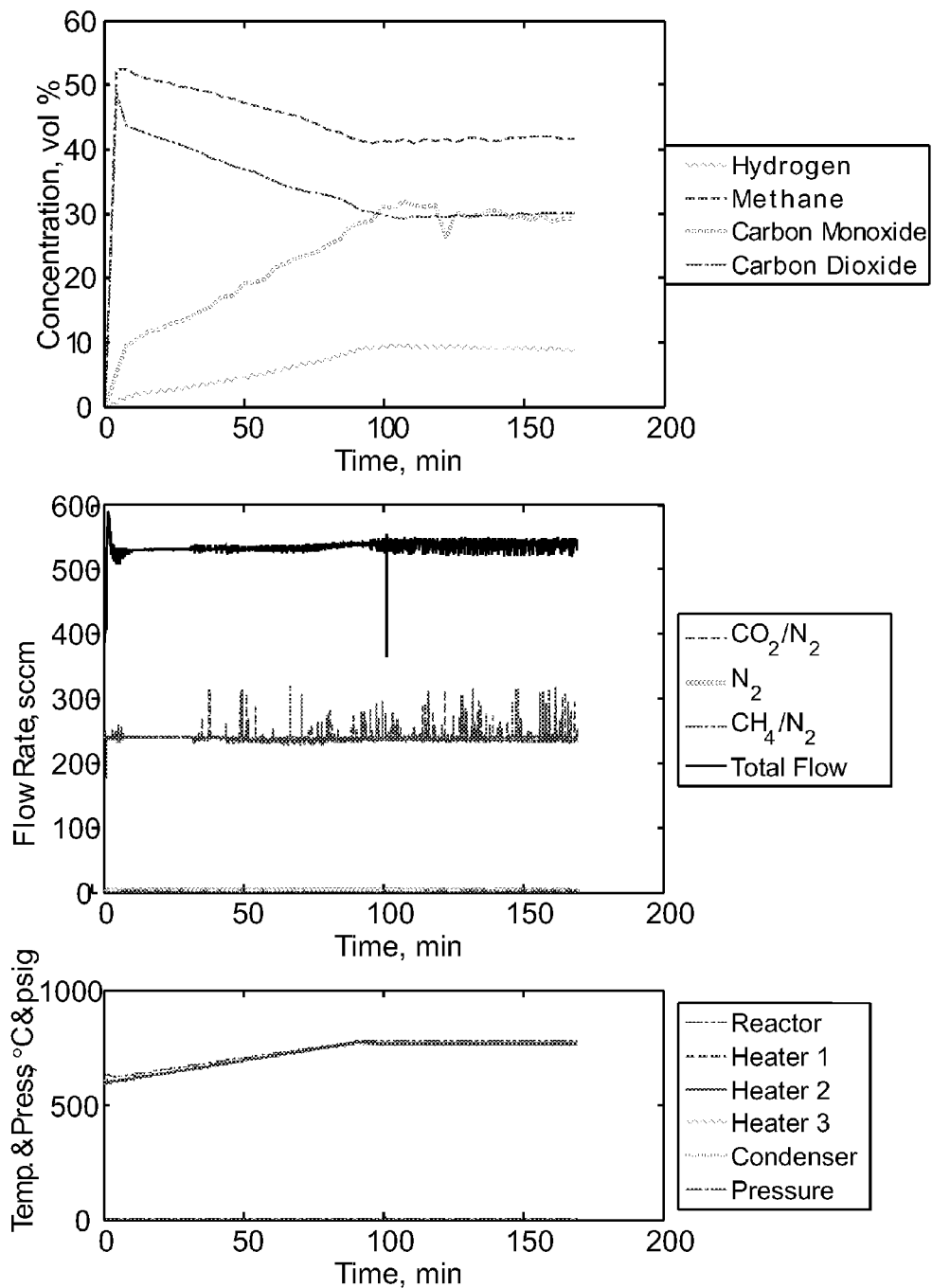

FIG. 24. At 1 bar (1:1 $CO_2$:$CH_4$) at 780° C. there is approximately 30 vol % CO and 10 vol % $H_2$.

Figure 25:
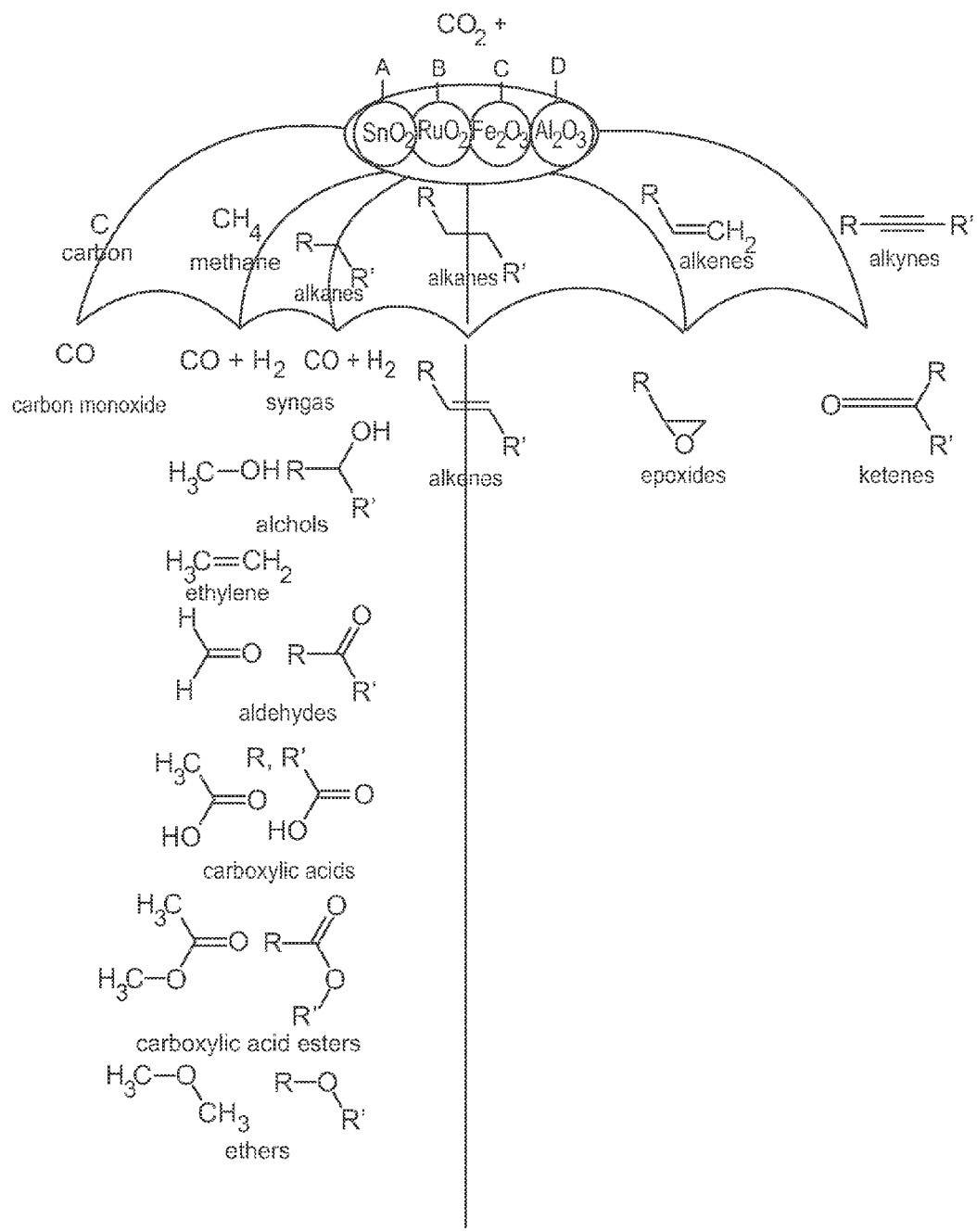

FIG. 25. A schematic showing non-limiting examples of the catalysis of (i) $CO_2$+C→2 CO and (ii) $CO_2$ used as an oxidant to produce a wide variety of industrially important organic chemicals.

5. DETAILED DESCRIPTION OF THE INVENTION

This invention provides specific mixed-metal oxides have been developed which can remove anoxygen from $CO_2$ and utilize the oxygen for the production of higher-value oxygenated, or oxidized, products. In their reduced forms, the mixed-metal oxides have been shown to remove oxygen from the strong carbon-oxygen bond of $CO_2$ (bond dissociation energy=~803 kJ/mol). The mixed-metal oxide is shown to facilitate transfer of the abstracted oxygen to other substrates and is catalytic in deoxygenation and oxygen transfer. The catalyst is shown to be able to transfer the abstracted oxygen to carbon-based reductants in several oxidation states such as carbon (C(s), e.g. pet coke), carbon monoxide (CO), and methane ($CH_4$). The catalyst will be useful for utilization of $CO_2$ for the production of $C_1$ oxygenate from pet coke and char, for the utilization of $CO_2$ as an oxygen source for selective hydrocarbon oxidations, dehydrogenations, and oxidative coupling, and for upgrading low-value hydrocarbons to higher-value or more useful products.

Several materials have been developed which catalyze the Reverse-Boudouard reaction for the production of CO from $CO_2$ and carbon in a reactor system operated at 800° C. We have shown conclusively that the catalyst materials operate by a catalyst-mediated extraction of oxygen from carbon dioxide to the reduced catalyst surface. The removal of oxygen from $CO_2$ is followed by transfer of the oxygen to a different carbon atom, and works for carbon in reduced oxidation states such as C(0), C(−2), or C(−4), as shown in FIG. 1.

The potential for the upgrading of carbon dioxide through industrial processes has been investigated over the course of the past one hundred years. Historically attractive energy applications have included production of methanol from $CO_2$ by methane reforming (Carnol process), methane production by hydrogenation of $CO_2$ (Sabatier reaction), and production of carbon monoxide and hydrogen by reforming $CO_2$ with methane. Carbon dioxide can be combined with carbon and transformed into carbon monoxide by the Reverse-Boudouard reaction in a reaction which is thermodynamically favored at high temperature (900° C.). Several researchers have explored catalysts for the Reverse-Boudouard reaction in the past. Among them, some have explored the oxidation and reduction of iron on elemental carbon supports and impregnated in coal. Alkali carbonates have also been used to catalyze char gasification by $CO_2$. Others have studied binary alkali-iron and alkaline-earth-iron mixed metal oxide systems and shown them to catalyze the formation of CO from carbon dioxide and chars. While other mixed metal oxides with nickel, ceria, and zirconia have been recently explored for carbon dioxide utilization by reforming to synthesis gas and by methanation, mixed metal oxides containing Group 8 metals and reducible oxides of p-block metals, specifically tin, have not been reported for the gasification of carbon with $CO_2$.

In one embodiment, this invention provides $SnO_2Fe_2O_3Al_2O_3$ as a catalyst family for deoxygenation of $CO_2$ and utilization of the oxygen from $CO_2$ with other carbon reductants to produce valuable chemicals and fuels.

The use of SnFeOx catalysts for deoxygenation of carbon oxygenates from biomass pyrolysis vapors has been disclosed in PCT/US2013/029379, the contents of which are hereby incorporated in its entirety.

This invention disclosure covers quaternary and even quintenary variations of the $Fe_2O_3(SnO_2)Al_2O_3$ catalyst formulation for $CO_2$ utilization. The most obvious additives are alkali and alkaline-earth metal promoters which can be added by many salt forms. Many variations were discovered, formulated, tested, and shown to work during this study.

This invention disclosure also covers a broad range of iron to tin to aluminum in the catalyst formulation, intended as all feasible ratios. Many variations were discovered, formulated, tested, and shown to work during this study.

This invention disclosure covers any formulation involving $Fe_2O_3(SnO_2)Al_2O_3$ calcined under all feasible calcination conditions. The catalysts may be useful for $CO_2$ utilization for CO production, char gasification, and selective oxidations of hydrocarbon reductants, oxidative methane coupling, oxidative dehydrogenation of light alkanes for olefin production, epoxidation of olefins to prepare alkeneoxides, preparation of methanol and dimethyl ether synthesis. The reagents disclosed herein may be used to produce additional commercially important products including but not limited to, acetic acid, acetic anhydride, ethylene vinyl acetate (EVA), styrene, terephthalic acid, formic acid, n-butanal, 2-methylpropanal, acrylic acids, neopentylacids, propanoic acid, dimethyl formamide, and Fischer-Tropsch hydrocarbons.

These important industrial materials can be used to manufacture a variety of finished goods, e.g., EVA for adhesives, glues, plastics, and foam rubber. EVA based consumer products include hot melt adhesives, glue sticks, plastic wraps, foam rubber, floats, fishing rods, shoes, and photovoltaics.

5.1. Compositions

As used herein the term "mixed transition metal iron (II/III) catalyst" means $Fe^{+2}$ or $Fe^{+3}$ mixed with a second metal which may be (i) a d-block element, IUPAC Groups 3-12; (ii) a "post-transition" metal (Al, Ga, In, Sn, Tl, Pb, Bi, Po); or an f-block element such as a lanthanide or actinide, sometimes referred as to as an "inner transition metal"; or a combination of (i), (ii) or (iii). The term mixed transition metal iron (II/III) catalyst includes the reagents disclosed herein. The term includes various oxidized forms of Fe including reactive species generated in situ such as $Fe^0$ or $Fe^{+1}$ in the catalyst. Mixed transition metal iron (II/III) catalysts are ionic materials; that is, they are materials that no longer retain metallic characteristics unlike metal alloys.

The invention provides compositions for the mixed transition metal iron oxide (II/III) catalysts. A non-limiting diagram of just some of the uses of the catalysts in shown in FIG. 25. The compositions can be described according to the formula ABCD, where each alphabetical letter indicates a set of metal oxides or mixed metal oxides from which one is selected and used with a member of another set. As few as two sets may be used, such as AC, BC, or DC. Also three sets may be used, such as ACD, ABC, or BCD. All four sets may be used, such as ABCD. Set C is only inclusive of iron.

The mixed transition metal may be a group A component, as exemplified by $SnO_2$. The group A component is involved in oxygen transport and $CO_2$ oxygen extraction. The group A components may also be: $BaCoO_3$, $Bi_2O_3$, $CaOZrO_2$, $CeO_2$, $Gd_2O_3$, $Gd_2Zr_2O_7$, $GdTi_2O_7$, $La_{1-y}Sr_yCoO_x$, $La_{1-y}Sr_yGa_{1-z}Mg_zO_x$, $La_2O_3$, $LaAlO_3$, $LaGaO_3$, $MgOZrO_2$, $Nd_2Zr_2O_7$, $NdGa_{1-y}Mg_yO_x$, $NdGaO_3$, $SmTi_2O_7$, $SrCoO_3$, $Y_2O_3ZrO_2$, $YTi_2O_7$, or $ZrO_2$.

Alternatively, the mixed transition metal may be a group B component, exemplified by $RuO_2$ and metal oxides. The group B components are involved in $CO_2$ oxygen extraction and hydrocarbon selective/partial oxidation. The group B components may also be: $AgO_2$, $CO_2O_3$, $CuO$, $La_{1-y}Sr_y$-$CoO_x$, $La_{1-y}Sr_yO_x$, $Mn_2O_3$, $Mn_2O_7$, $Mn_3O_4$, $MnO$, $MnO_2$, $MoO_3$, $Re_2O_7$, or $V_2O_5$.

The group C component is exemplified by $Fe_2O_3$. The group C component is involved in oxygen transport and $CO_2$ oxygen extraction. The group D component is a support for the mixed transition metal iron catalysts which is exemplified by $Al_2O_3$. One of ordinary skill in the art would recognize additional supports. The components of group D may be $Al_2O_3$, $Al_2O_3$—$SiO_2$, $CaAl_2O_4$, $CaOZrO_2$, $K_2Al_2O_4$, $MgAl_2O_4$, $MgOZrO_2$, $Na_2Al_2O_4$, $SiO_2$, $TiO_2$, $Y_2O_3ZrO_2$, or $ZrO_2$. Other, non-catalyst heat transfer media also can be used, such as alumina, silica, olivine, and sands.

Furthermore, the catalysts may also include a promoter which will act to lower the work function or suppress sintering and/or coking. The promoter components may be a compound having the formula $A_2O$; $A_2CO_3$; or $A(OH)$ (where A=Na, K, Cs); BO; $BCO_3$; $B(OH)_2$ (where B=Mg, Ca, Sr); or a mixture of A and B compounds.

In one embodiment, the mixed transition metal iron (II/III) catalyst may have the formula $Fe_2O_3(SnO_2)_{0.1-10}(Al_2O_3)_{0.1-10}$. In alternative embodiments, the mixed transition metal iron (II/III) catalyst may have the formula $Fe_2O_3(SnO_2)_{0.2-5.0}(Al_2O_3)_{0.2-5.0}$, $Fe_2O_3(SnO_2)_{1.0-2.0}(Al_2O_3)_{0.5-5.0}$, $Fe_2O_3(SnO_2)_{0.5-5.0}(Al_2O_3)_{1.0-3.0}$, $Fe_2O_3(SnO_2)_{1.0-3.0}(Al_2O_3)_{1.0-3.0}$, $Fe_2O_3(SnO_2)_{1.0-2.5}(Al_2O_3)_{1.0-2.5}$, or $Fe_2O_3(SnO_2)_{1.2-2.2}(Al_2O_3)_{1.2-2.2}$.

The mixed transition metal iron (II/III) catalyst may have the formula $(RuO_2)_{0.001-0.2}Fe_2O_3$. Alternatively, it may have the formula $(RuO_2)_{0.002-0.1}Fe_2O_3$, $(RuO_2)_{0.005-0.05}Fe_2O_3$, $(RuO_2)_{0.008-0.02}Fe_2O_3$, $(RuO_2)_{0.01-0.02}Fe_2O_3$.

Table 1 shows compounds that were prepared and their reaction temperatures.

| Metal Oxide | Reduction Temperature Range ($H_2$, °C.) | Reduction Temp. Range (CO, °C.) | Reduction Capacity (CO, wt %) | Oxidation Temp. ($CO_2$) |
|---|---|---|---|---|
| $La_2O_3$ SrOCoO $Fe_2O_3$ | 250-550 | 400-490 | 4 | 200-500 |
| $MnO_2$ $Fe_2O_3$ | 400-450 | 300-450 | 11.7 | 250-450 |
| $(K)_{0.1}((Mg)_{0.1}((CuO)_{0.38}(Fe_2O_3)_{0.29}(Al_2O_3)_{0.33}))$ | 300-370 | 150-550, 700-800 | 6.7 | 350-450 |
| (CuO)0.38(Fe2O3)0.29(Al2O3)0.33 | 150-230 | 100-400 | 8.8 | — |
| $(RuO_2)_{0.024}Fe_2O_3$ | 225-265, 350-775 | 250-425 | 19.9 | 350-450 |
| $(RuO_2)_{.049}Fe_2O_3$ | 225-270, 400-850 | 225-425 | 19.3 | 350-450 |
| $(RuO_2)_{.012}Fe_2O_3$ | 230-290, 400-900 | 230-400 | 21.2 | 360-450 |

-continued

| Metal Oxide | Reduction Temperature Range ($H_2$, °C.) | Reduction Temp. Range (CO, °C.) | Reduction Capacity (CO, wt %) | Oxidation Temp. ($CO_2$) |
|---|---|---|---|---|
| $RuO_{0.024}Fe_2O_3$ | 225-245, 400- | 225-425, | 16.3 | 350-450 |
| $(Fe_2O_3)_{0.56}(SnO_2)_{0.78}Al_2O_3$ | | 225-400, 475-800 | 16.8 | 600-800 |
| $(K)_{.001}(Mg)_{.0025}(Fe_2O_3)_{0.56}(SnO_2)_{0.78}Al_2O_3$ | 590-650 | 225-400, 475-800 | 16.8 | 650-800 |
| $(K)_{0.15}(Mg)_{0.1275}((Fe_2O_3)_{0.56}(SnO_2)_{0.78}Al_2O_3)_{0.7225}$ | 550-725 | 525-800 | 12 | 400-775 |
| $(MnO_2)_{0.2}(ZnO_2)_{0.8}Fe_2O_3$ | 600-675 | 250-450 | 15 | 650-700 |

The reduction temperatures are the range of temperatures at which the materials can be reduced by hydrogen gas or carbon monoxide gas to make reactive reduced catalysts. The reduction capacity is the percentage of the mass which is decreased by the removal of oxygen from the catalyst. The oxidation temperature is the temperature range in which the reduced material is reoxidized by carbon dioxide.

The catalytic reaction can be carried out in a variety of different types of reactors. Preferably, the reactor is a fluid-type reactor, such as a fluidized bed or a transport reactor. In one embodiment, a riser reactor may be used. The $CO_2$ and carbon and/or organic starting materials may be provided to the reactor at a defined rate—e.g., a rate such that the residence time is less than defined time, such as about 5 seconds or less.

Preferably, the reactor used is one that is capable of achieving the necessary conditions to form a specific reaction product. Specifically, it can be beneficial to use a reactor that is adapted for relatively short residence times of the reactants and the catalyst in the reactor, as noted above.

Another condition to be considered is reaction temperature. In specific embodiments, the reacting of the $CO_2$ and carbon and/or organic starting materials in the presence of the catalyst can be carried out at a temperature of about 200° C. to about 900° C., about 300° C. to about 700° C., about 350° C. to about 600° C., about 400° C. to about 500° C. or a temperature of about 550° C. or less. In other embodiments, the reacting of the $CO_2$ and carbon and/or organic starting materials can be carried out at a pressure of up to about 25 bar (2.5 MPa) or about 80 bar (8.0 MPa). In some embodiments, reacting can be carried out at ambient pressure to near ambient pressure.

The process of the disclosure can comprise separation of the products into two or more different fractions. This can comprise transferring the stream comprising the product(s) to a separator. In some embodiments, the stream may be separated into a vapor and gas fraction and a solids fraction, which comprises solid reaction products and the catalyst. The inventive method also can comprise regenerating and recycling the catalyst into the pyrolysis process. In some embodiments, this also may include transferring the catalyst from the separator through a reducing zone prior to re-introduction into the reactor.

Unless defined otherwise, all technical and scientific terms used herein have the same meaning as commonly understood by one of ordinary skill in the art to which this invention belongs. The article "a" and "an" are used herein to refer to one or more than one (i.e., to at least one) of the grammatical object(s) of the article. By way of example, "an element" means one or more elements.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. The present invention may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

The following Examples further illustrate the invention and are not intended to limit the scope of the invention. In particular, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

6. EXAMPLES

6.1. Mixed Tin Iron Oxides for Carbon Dioxide Utilization

The use of $CO_2$ as a chemical feedstock is an appealing strategy for reducing greenhouse gas emissions especially if technologies currently being developed to remove $CO_2$ from fossil fuel fired power plant exhaust gases lead to abundant, high purity, carbon dioxide feedstocks.[1] If the $CO_2$ gas streams can be used as reactants in processes which yield more energetic products, such as a fuel or value-added intermediate, then the original carbon in the fossil fuel would be recovered for utilization in another application.[2,3] The potential for the upgrading of carbon dioxide through industrial processes has been investigated for the past one hundred years.[4] Historically attractive energy applications have included methane production by hydrogenation of $CO_2$ (Sabatier reaction), production of carbon monoxide and hydrogen by reforming $CO_2$ with methane (dry methane reforming), production of methanol from $CO_2$ by methane reforming (Carnol process), and gasification of chars using $CO_2$ to make CO (Reverse-Boudouard reaction).[5-8]

In the Reverse-Boudouard reaction, the transformation becomes thermodynamically favoured beginning at ~700° C. but conversion is low below ~900° C. Several researchers have explored catalysts for the Reverse-Boudouard reaction in the past and have been reviewed by several authors.[4, 9-21] The goal of catalysis is to increase the reaction rate at lower temperature. Among them, some have explored the oxidation and reduction of iron on elemental carbon supports and impregnated in coal using techniques such as thermogravimetric analysis, $^{13}CO_2$ pulsed reactions, and temperature programmed desorption.[13, 15, 22, 23] Alkali carbonates have also been found to catalyse char gasification by $CO_2$ and some researchers have studied binary alkali-iron and alkaline-earth-iron mixed metal oxide systems and shown them to catalyse the formation of CO from carbon dioxide and chars.[24-30] Recently mixed metal oxides with nickel, ceria, and zirconia have been explored for carbon dioxide utilization by reforming to synthesis gas and by methanation.[31-33] To our knowledge, mixed metal oxides containing Group 8 metals and reducible oxides of p-block metals, specifically tin, have not been reported for the gasification of carbon with $CO_2$. However, until now, little work has been done to show conclusively that the oxygen extracted from $CO_2$ by the catalyst materials results in transfer of the extracted oxygen to an external carbon source rather than incorporation of the oxygen into the catalyst structure. We have developed mixed metal oxides of tin and iron which catalyze the Reverse-Boudouard reaction for production of CO from carbon feedstocks such as pet-coke and biomass char. In this disclosure we characterize the removal of oxygen from $CO_2$ by a reduced tin-iron catalyst and show that the oxygen comes from carbon dioxide and is transferred to other carbon sources as shown in FIG. 1. The reaction was studied using isotopically-labeled $C^{18}O_2$, thermogravimetric analysis, and mass spectroscopy. The results show that the highly stable carbon-oxygen bonds of $CO_2$ can be broken with subsequent transfer of the oxygen to a carbon atom of lower oxidation state. One of ordinary skill will be able modify the catalyst formulations disclosed herein to make formulations which abstract oxygen from $CO_2$ at lower temperatures and catalysts which can selectively or partially oxidize other carbon-based reductants leading to higher-value products. Furthermore, the utilization of $CO_2$ to feed oxygen to catalysts in partial-oxidation processes which currently use oxygen separation units has the potential to lower capital costs for processes while providing additional markets for captured carbon dioxide beyond conventional enhanced oil recovery applications.

Mixed metal oxides containing tin are composed of tin-oxide phases which are known to have temperature-induced oxygen mobility.[34, 35] In considering the $SnO_2Fe_2O_3Al_2O_3$ catalyst formulation and the given reaction conditions, it is sensible to question what types of oxygen containing sites are involved in the reduction of carbon dioxide and to consider the extent of oxygen transfer synergies. One simplistic perspective is to consider the oxygen in the catalyst associated with $SnO_2$ as distinct from the oxygen which is associated with $Al_2O_3$ and likewise for the oxygen associated with $Fe_2O_3$. The nominal formulation of the catalyst investigated here is $(Fe_2O_3)(SnO_2)_{1.41}(Al_2O_3)_{1.82}$ and is given in FIGS. 1 and 2 along with a proposed mechanism which broadly describes a pathway for oxygen transfer. This mechanistic hypothesis can be tested by Thermogravimetric analysis (TGA). For example, the weight loss observed for loss of oxygen exclusively from $SnO_2$ (8.1% theoretical observed for all the oxygen in the catalyst). The theoretical limit to the weight loss due to complete oxygen loss is 32.4%. Intermediate weight losses could correspond to loss of oxygen from a combination of $SnO_2$ and $Fe_2O_3$ (16.7%), or only $Fe_2O_3$ (8.6%), or even by incomplete reduction of $Fe_2O_3$ to FeO (5.7%).

Since the thermogravimetric analyses shown in FIG. 3 shows the total weight loss to be only approximately 21.6%, it is not possible that all the oxygen in the materials is available to reduction. Similarly, since an overall weight loss of 21.6% is observed starting from ambient, it is not likely that the oxygen originates exclusively from $SnO_2$ or exclusively from $Fe_2O_3$ given the elemental analysis (Supplementary Information, Sec. 6.3. below). FIG. 3 shows that the overall weight loss observed from ambient is approximately 21.6%. Approximately 7.4% of the initial weight is lost upon heating the sample to 800° C. in nitrogen (dark grey, inert). Presumably, this corresponds to loss of surface adsorbed and absorbed species such as adventitious water, oxygen, or carbon dioxide. Further changes in weight are described relative to the sample weight following the initial desorption as suggested by the four horizontal lines on the weight profile.

Following the inert thermal ramp, the weight of the sample is further decreased when the material is again heated to 800° C. in the presence of 10% CO ($N_2$ balance, white). The weight loss due to reduction by CO is approximately 15.4%. Subsequent oxidation with $CO_2$ results in a weight gain of about 99.1% of the previous weight loss (light grey). Following the treatment with $CO_2$ about 0.5% of the initial weight is lost by ramping to 800° C. in nitrogen. When the catalyst is again treated with CO in a second reduction step, a smaller weight loss (~13.3%) is observed compared to the first reduction step. This is consistent with irreversible transition from mixed valent $Fe_2O_3$ to lower valent $Fe_3O_4$, a transition which accounts for approximately 3.4 wt % change due to oxygen loss. It is also consistent with the hypothesis that some catalyst is lost to deactivation, either reversible, or irreversible. One reversible catalyst deactivation route is the forward Boudouard Reaction, where one equivalent carbon is deposited from the disproportionation of two equivalents of CO. A follow-up oxidation step leads to a weight gain equal in magnitude to the weight loss observed during the previous reduction. A slight weight gain is then observed when the oxidized catalyst is further oxidized while heated to 800° C. in air, returning the sample to approximately the same weight observed after the initial desorption. After air oxidation, reduction with CO shows a 14.0% weight loss.

In a follow-up experiment (Supplementary Information, Sec. 6.3 below), the catalyst was reduced again with CO after two cycles then oxidized with air. It showed a return to the weight observed prior to all reduction steps and at the end of each oxidation step. This comparison shows that the catalyst can obtain oxygen from $CO_2$, a relatively poor oxidant, almost as effectively as it can from $O_2$, a relatively strong oxidant.

Overall, the weight changes observed in the thermogravimetric analyses in the absence of a reductant are most likely due to desorption of adventitious adsorbates ($H_2O$, $CO_2$, possibly $O_2$) from the surface of the catalyst. In the presence of a reductant, both $SnO_2$ and $Fe_2O_3$ sites are reduced when heated to 800° C., but $Al_2O_3$ sites do not appear to be reduced. The observed weight loss (15.5%), agrees well with the amount of oxygen calculated to be associated with $SnO_2$ and $Fe_2O_3$ (16.7%).

It must be noted that the thermogravimetric analysis cannot be used to conclusively rule out coincidental weight changes resulting from combinations of partial oxygen losses from $SnO_2$, $Fe_2O_3$, and $Al_2O_3$ sites. However, FIG. 4 shows plots of the observed weight changes with temperature purge gas over the temperature range from 0-800° C. Each weight change trace is numbered for distinction. The derivative plots indicate that changes in weight are likely due to three events and involve two types of active catalytic sites. The weight change observed during the initial temperature ramp in nitrogen (black) peaks distinctly at 100° C. in agreement with the hypothesis that the initial weight loss involves the loss of adventitious absorbates. When the reduced catalyst is oxidized by treatment with $CO_2$ (dashed traces), two separate events are observed to occur, the first at approximately 650° C. and the second occurring at approximately 720° C. The bimodal distribution for weight change under oxidizing conditions is reproducible in both $CO_2$ treatment steps. These observations are consistent with oxygen abstraction from $CO_2$ occurring at two different sites, one active at slightly lower temperature than the other. In the reduction steps, a bimodal distribution is also observed. A low temperature weight change is observed at approximately 400° C. and is minor compared to the higher temperature weight change observed at 700° C. A third minor weight change is also observable above 700° C. but is not as pronounced as the primary peak. It is also observed that in the initial reduction cycle, weight changes are observed at slightly lower temperatures compared to the next two cycles. This could indicate that an irreversible transition is made on the active site during the first reduction. This would be consistent with the transition of $Fe_2O_3$ to $Fe_3O_4$, with the reduction of mixed oxide Fe (III)/Fe (II) anticipated to be easier than the reduction of a more reduced Fe(II)/Fe(III). Lastly, the sample is treated with air (- - -) after the catalyst has been oxidized with $CO_2$, and there is little observable change in weight during this event.

Mass spectroscopy (MS) experiments were conducted with isotopically labelled $C^{18}O_2$. The study reveals details about both the fate of the oxygen abstracted from $CO_2$ as well as the capability of the catalyst to transfer metal-oxide-associated oxygen to external carbon sources. Details of the experiment are provided in the Supplementary Information (Sect. 6.3). In short, gas exiting a fixed-bed catalyst zone was analysed by MS. Isotopically-labelled $C^{18}O_2$, was used to follow oxygen through the reaction and shows the original molecular connectivity and the molecular connectivity of the products. In the presence of a catalyst which abstracts oxygen from carbon dioxide, heavy oxygen ($^{18}O$) will be removed and $C^{18}O$ will be produced as the primary product. We anticipated observing this by MS upon treatment of the reduced catalyst with $C^{18}O_2$. It was surmised that this would label the reduced catalyst with $^{18}O$ and that the labelled catalyst could then be reduced again with CO with the resulting production of $C^{16}O^{18}O$ as shown in FIG. 5.

The experimental results are shown below in FIG. 6 with the observed mass signals (lower) correlated to the reactor temperature (upper) and purge gas (by shade). The most relevant segments are the first oxidation segment (light grey), where oxygen is removed from $C^{18}O_2$, and the last reduction section (white), where CO removes oxygen from the catalyst. FIG. 6 shows that initial reduction with CO (first white segment) gives an increase in mass 44 at approximately 800° C. which corresponds to production of $CO_2$ using unlabelled oxygen from the catalyst. In the reduced state, the catalyst removes oxygen from $C^{18}O_2$ at approximately 650° C. as shown. The decrease in the signal intensity of $C^{18}O_2$ is accompanied by corresponding increases in $C^{18}O$, but also unexpectedly by an increase in $CO^{18}O$, which indicates three potential scenarios. One, labelled oxygen is coupled to surface bound CO from the previous step. Second, unlabelled oxygen from the catalyst surface is coupled to $C^{18}O$ before it is dissociated from the catalyst surface. Third, carbon is deposited on the catalyst surface during the preceding reduction step and gets coupled to one unlabelled oxygen and one labelled oxygen. All three scenarios require removal of $^{18}O$ from $C^{18}O_2$ and show the capability of the material to utilize oxygen from carbon dioxide.

In the fourth step, the labelled catalyst was again treated with flowing 20% CO. Here we anticipated observing a decrease in CO and a corresponding increase in $CO^{18}O$ associated with reduction of the catalyst by removal of $^{18}O$ which the catalyst abstracted from $C^{18}O_2$. Indeed there is this correlation, however, as FIG. 7 shows, we also observed the formation of all the other species which can be proposed to involve surface bound oxygen ($CO^{18}O$, $CO_2$, $C^{18}O$, $C^{18}O_2$). The observation of all species correlated to the decrease in the CO signal. The appearance of $CO^{18}O$ supports the hypothesis that heavy oxygen ($^{18}O$) is abstracted from $C^{18}O_2$ by the catalyst, and then added to a different carbon source, in this case carbon monoxide, to produce partially labelled carbon dioxide ($CO^{18}O$). The observation of $CO_2$ may be primarily from incomplete labelling of the catalyst in the prior oxidation step. The time dependent decrease in signal intensity for $CO^{18}O$ but not $CO_2$ is consistent with consumption of labelled oxygen from the surface of the catalyst over time. The observation of $C^{18}O$ was unanticipated, but shows that carbon monoxide may undergo disproportionation to carbon and carbon dioxide with carbon deposition on the catalyst surface where it picks up an $^{18}O$ from the labelled catalyst. It is conceivable that carbon monoxide is absorbed on the surface of the catalyst, deoxygenated, and then reoxygenated with a labelled $^{18}O$. The detection of $C^{18}O_2$ can only be accounted for by mechanistic routes which involve labelling of the catalyst with $^{18}O$ in the previous oxidation step followed by transfer of the labelled oxygen during the subsequent reduction step, either to a carbon which is absorbed by the catalyst as CO before undergoing oxygen metathesis and oxygen addition, or to a carbon which is deposited on the catalyst as elemental carbon before undergoing two oxygen additions with labelled $^{18}O$ which must have originated from labelled $C^{18}O_2$.

In summary, the mechanistic investigation of the $CO_2$ utilization catalyst $Fe_2O_3(SnO_2)_{1.41}(Al_2O_3)_{1.82}$ has been conducted and results obtained from mass spectroscopy experiments using isotopically-labelled carbon dioxide prove that the reduced catalyst abstracts oxygen from carbon dioxide and transfers it to another carbon. Thermogravimetric evidence suggests that oxygen from $Fe_2O_3$ and $SnO_2$ are mobile and able to be removed from the catalyst by reductant. Rapid exchange of oxygen by the catalyst easily occur due to the observed high mobility of oxygen between the catalyst and carbon dioxide which may lead to potential side reactions.

6.2. References for Section 6.1 (Mixed Tin Iron Oxides)
1. P. Markewitz, W. Kuckshinrichs, W. Leitner, J. Linssen, P. Zapp, R. Bongartz, A. Schreiber and T. E. Muller, *Energy & Environmental Science*, 2012, 5, 7281-7305.
2. M. B. Ansari and S.-E. Park, *Energy & Environmental Science*, 2012, 5, 9419-9437.
3. N. A. M. Razali, K. T. Lee, S. Bhatia and A. R. Mohamed, *Renewable & Sustainable Energy Reviews*, 2012, 16, 4951-4964.
4. M. Halmann and M. Steinberg, *Greenhouse Gas Carbon Dioxide Mitigation Science and Technology*, Lewis Publishers, Washington, D. C., 1999.
5. K. Nagase, T. Shimodaira, M. Itoh and Y. Zhemg, *Physical Chemistry Chemical Physics*, 1999, 1, 5659-5664.
6. M. Steinberg, Brookhaven National Lab, Upton, N.Y., December 1995.
7. S. K. Hoekman, A. Broch, C. Robbins and R. Purcell, *International Journal of Greenhouse Gas Control*, 2010, 4, 44-50.
8. F. Fischer and H. Tropsch, *Brennst. Chem.*, 1928, 9, 29-46.
9. S. Yokoyama, K. Miyahara, K. Tanaka, I. Takakuwa and J. Tashiro, *Fuel*, 1979, 58, 510-513.
10. T. Suzuki, H. Ohme and Y. Watanabe, *Energy and Fuels*, 1994, 8, 649-658.
11. F. Carrasco-Marin, J. Rivera-Utrilla, E. U. Hidalgo and C. Moreno-Castilla, *Fuel*, 1991, 70, 13-16.
12. A. P. Dhupe, A. N. Gokarn and L. K. Doraiswamy, *Fuel*, 1991, 70, 839-844.
13. H. Ohme and T. Suzuki, *Energy and Fuels*, 1996, 10, 980-987.
14. F. Akiyama, *Chemistry Letters*, 1997, 643-644.
15. T. Kodama, S. Miura, T. Shimuzu, A. Aoki and Y. Kitayama, Abstr. 4th Int. Conf. on Carbon Dioxide Utilization, Kyoto, Japan, 1997.
16. R. T. Yang and C. Wong, *Journal of Catalysis*, 1983, 82, 245-251.
17. K. J. Huttinger and O. W. Fritz, *Carbon*, 1991, 29, 1113-1118.
18. H. Ono, M. Kawabe, H. Amani, M. Tsuji and Y. Tamaura, Abstracts of the Fourth International Conference on Carbon Dioxide Utilization, Kyoto, Japan, September, 1997, P-004.
19. M. Steinberg and Y. Dong, Abstracts of the International Conference on *Carbon* Dioxide Utilization, Bari, Italy, September 1993.
20. M. Steinberg, Abstracts of the Third International Conference on Carbon Dioxide Utilization, Norman, Okla., May, 1995.
21. B. J. Wood and K. M. Sancier, *Catalysis Reviews-Science and Engineering*, 1984, 26, 233.
22. T. Suzuki, K. Inoue and Y. Watanabe, *Energy and Fuels*, 1988, 2, 673.
23. T. Suzuki, K. Inoue and Y. Watanabe, *Fuel*, 1989, 68, 626.
24. J. M. Saber, J. L. Falconer and L. F. Brown, *Fuel*, 1986, 1356.
25. J. M. Saber, J. L. Falconer and L. F. Brown, *Journal of the Chemical Society, Chemical Communications*, 1987, 445.
26. S. R. Kelemen and H. Freund, *Carbon*, 1985, 23, 723.
27. S. Yokoyama, K. Miyahara, K. Tanaka, J. Tashiro and I. Takakuwa, *Journal of the Chemical Society of Japan*, 1980, 6, 974.
28. T. Suzuki, M. Mishima and Y. Watanabe, *Chemistry Letters*, 1982, 985.
29. J. Carrazza, W. T. Tyose, H. Heinemann and G. A. Somorjai, *Journal of Catalysis*, 1985, 96, 234.
30. Y. Ohtsuka, K. Hosoda and Y. Nishiyama, *Journal of the Fuel Society of Japan*, 1987, 66, 1031.
31. M. B. Gawande, R. K. Pandey and R. V. Jayaram, *Catalysis Science and Technology*, 2012, 2, 1113-1125.
32. P. Kumar, Y. Sun and R. O. Idem, *Energy and Fuels*, 2008, 22, 3575.
33. F. OCampo, B. Louis and A. Roger, *Applied Catalysis a-General*, 2009, 369, 90.
34. J. Maier and W. Gopel, *Journal of Solid State Chemistry*, 1988, 72, 293-302.
35. J. Mizusaki, H. Koinuma, J.-I. Shimoyama, M. Kawasaki and K. Fueki, *Journal of Solid State Chemistry*, 1990, 88, 443-450.

6.3. Supplemental Information on Mixed Tin Iron Oxides for Carbon Dioxide Utilization Synthesis of $Fe_2O_3(SnO_2)_{1.41}(Al_2O_3)_{1.82}$ Catalyst The mixed oxide catalyst was obtained by co-precipitation of metal salts from aqueous solutions using conventional procedures. Tin (IV) chloride, pentahydrate (Sigma Aldrich, 98%), iron (III) nitrate, nonahydrate (Sigma Aldrich, ≥98%), aluminum nitrate, nonahydrate (Sigma Aldrich, ≥98%) and ammonium hydroxide (BDH Aristar, 28-30%), were obtained and used as received without further purification.

The catalyst was prepared according to the following procedure: 172.24 g (0.491 mole) $SnCl_4.5H_2O$, 281.24 g (0.696 mole) $Fe(NO_3)_3.9H_2O$, and 476.81 g (1.271 mole) $Al(NO_3)_3.9H_2O$ were dissolved into a beaker containing 1620 g of deionized $H_2O$ by mixing for at least 1 hour. The salt solution was added at a constant rate of 30 mL/min to a tank containing 1500 g of DI water. A solution of $NH_4OH$ (504.07 g, 4.17 mole) in DI $H_2O$ was added at a variable rate of 8-10 mL/min to maintain the pH of the precipitation at 8.0±0.2. The precipitation was stopped when all the metals salts were added to the precipitation tank and the pH was equal to 8.0. The precipitation was allowed to mix for an additional 45 minutes. The precipitate was filtered into two wet cakes and then washed with DI water until the eluent contained chloride ion, as detected by a solution of 0.1M $Ag(NO_3)_2$, at a ppb level (based on $K_{sp}$). An LOI of each cake was used to determine the solid metal oxides content of each cake. By calculation, 195.3 g solids were obtained, >99% yield. Elemental analysis by ICP-MS showed Fe 18.7%, Sn 28.0%, Al 16.6%, theory Fe 20.3%, Sn 30.2%, Al 17.4%.

Thermogravimetric Analysis

Thermogravimetric analysis (TGA) was conducted using TA Instruments TGA Q500 with Advantage for Q Series software. The plumbing of the TGA furnace was altered to receive gas for the sample purge from external mass flow controllers (MFCs), operated via an electronic control box. This allows for the selection of additional gases for the sample purge compared to the standard Q500 design. Switching between gases was performed manually via in-line two-way valves, and flows were set according to MFC calibrations for each gas. Two temperature programs were used involving multiple steps to demonstrate the addition and removal of oxygen from the surface of the catalyst. For each analysis, a fresh sample (20-30 mg) was loaded in a tared, platinum TGA pan at the start of the program. Each program extended over multiple days, and the same sample was used for the duration. When necessary, the sample was held overnight or over-weekend in the closed TGA furnace under nitrogen at room temperature. In short, both programs describe heating the sample to 800° C. and soaking for 60 minutes before cooling back down to 30° C. using different gases to observe reducing, oxidizing, or purely thermal effects. In both programs, two cycles of the following steps are carried out. Thermal desorption is first observed followed by reduction, then oxidation with $CO_2$, again thermal desorption, then reduction, and oxidation with $CO_2$. In one program, the final oxidation with $CO_2$ is followed by oxidation with air, to observe any sites which may require a stronger oxidant than $CO_2$. In the second program, the second oxidation with $CO_2$ is followed by another reduction step, then oxidation with air, to confirm that the weight gain from the reduced sites oxidized in air is the same as the weight gain observed for oxidation of the reduced sites by carbon dioxide.

AutoChem-MS Analysis with Isotopically—Labelled Gases

A Micromeritics' AutoChem II 2920 Chemisorption Analyzer was interfaced with a Dycor Quadrupole Mass Spectrometer and used to follow the transformations of carbon dioxide, carbon monoxide, and oxygen. The AutoChem II 2920 is a fully automated instrument capable of conducting precise chemical adsorption and temperature programmed reaction studies. The sample is contained in a quartz reactor housed in a clamshell furnace, programmable up to 1100° C. Four gas inlets with high-precision, independently calibrated mass flow controllers provide accurate delivery of up to four analysis gases over the course of an experiment. For these experiments, the AutoChem was operated with constant flow of analysis gas through the sample reactor. Gases employed were ultra-high purity helium, a certified mixture of 20% CO in helium, and either $^{13}C$ or $^{18}O$ labelled $CO_2$. The Isotopically-labelled gases were purchased from Sigma-Aldrich and used as received. Experimental conditions for an exemplary experiment are given in Table 2 below. The results are given in Results and Discussion Section below.

TABLE 2

Exemplary parameters for $SnO_2Al_2O_3(Fe_2O_3)_3$ testing for $^{12}C^{18}O_2$ oxygen abstraction.

| Step | Temp 1 (° C.) | Temp 2 (° C.) | Temperature Ramp Rate (° C./min) | Gas | Flow (mL/min) | Hold Time (min) |
|---|---|---|---|---|---|---|
| 1 | 40 | 40 | 0 | CO/He | 15 | 5 |
| 2 | 40 | 800 | 10 | CO/He | 15 | 5 |
| 3 | 800 | 40 | 50 | CO/He | 15 | 5 |
| 4 | 40 | 40 | 0 | $N_2$ | 15 | 5 |
| 5 | 40 | 40 | 0 | $^{12}C^{18}O_2$ | 15 | 5 |
| 6 | 40 | 800 | 10 | $^{12}CO_2$ | 15 | 5 |
| 7 | 800 | 40 | 50 | $^{12}CO_2$ | 15 | 5 |
| 8 | 40 | 40 | 0 | $N_2$ | 15 | 5 |
| 9 | 40 | 800 | 10 | $N_2$ | 15 | 5 |
| 10 | 800 | 40 | 50 | $N_2$ | 15 | 20 |

Treatment of Reduced Catalyst with Air

In a thermogravimetric experiment described herein, a program was used to evaluate the weight loss and weight gain shown by $(Fe_2O_3)(SnO_2)_{1.41}(Al_2O_3)_{1.82}$ when it was heated to 800° C. while being reduced with 10% CO (white) followed by oxidation with 100% $CO_2$ (light grey). After two cycles the catalyst was reduced again with 10% CO (white), and then oxidized with air (lighter grey). The weight of the reduced catalyst after oxidation with $CO_2$ was the same as the weight of the reduced catalyst after oxidation with $O_2$. Experimental results of the experiment are given in FIG. 8.

Plots of the observed weight changes with temperatures corresponding to the experiment described above are shown in FIG. 9. The data is displayed by purge gas over the temperature range from 0-800° C., thus for most weight changes observed when ramping to 800° C. there is a corresponding static weight observation for cooling from 800° C. Each weight change trace is numbered to indicate that it is associated with a different step in the TGA program. The derivative plots indicate that changes in weight are likely due to three events and involve two types of active catalytic sites. The weight change observed during the initial temperature ramp in nitrogen (black) peaks distinctly at 100° C. in agreement with the hypothesis that the initial weight loss involves the loss of adventitious absorbates. When the reduced catalyst is oxidized by treatment with $CO_2$ (red traces), two separate events are observed to occur, the first at approximately 650° C. and the second occurring at approximately 720° C. The bimodal distribution for weight change under oxidizing conditions is reproducible in both $CO_2$ treatment steps. These observations are consistent with oxygen abstraction from $CO_2$ occurring at two different sites, one active at slightly lower temperature than the other. In the reduction steps (dashed line), a bimodal distribution is also observed. A low temperature weight change is observed at approximately 400° C. and is minor compared to the higher temperature weight change observed. Catalyst oxidation by $O_2$ (air)(-- -) occurs at lower temperatures (~100-400° C.) compared to $CO_2$ (~650-750° C.). This also shows the relative strengths of $O_2$ and $CO_2$ as oxidants and affinity of the catalyst for $O_2$ relative to $CO_2$.

In summary, the AutoChem-MS studies using isotopically labeled $C^{18}O_2$ yield strong evidence in support of the hypothesis that $Fe_2O_3(SnO_2)_{1.41}(Al_2O_3)_{1.82}$ removes oxygen from $CO_2$ and transfers it to other carbon sources. The appearance of $C^{18}O$ and $C^{16}O^{18}O$ during oxidation of the reduced catalyst with $C^{18}O_2$ shows the capability of the catalyst to abstract oxygen from carbon dioxide as well as the ability to transfer catalyst-ligated oxygen to an external carbon source. The appearance of $C^{16}O^{18}O$, $C^{18}O$, and $C^{18}O^2$ during reduction of the $^{18}O$ labeled oxidized catalyst shows the ability of the catalyst to transfer ligated oxygen's to carbon sources. It is clear that in addition to the transformations which occur on the desired reaction pathway, numerous other transformations occur in side routes on the same time scale. FIG. 10 depicts a mechanism which could account for the events observed under the experimental conditions used in the mass spectroscopy study. Starting from top and moving clockwise, the catalyst precursor is activated by reduction with CO producing $CO_2$ and vacancies in the coordination sphere of the active site. The active sites are occupied by oxygen of $CO_2$ and CO is produced (top right corner). Oxygen from $CO_2$ is combined with CO to make $CO_2$ again and regenerate coordinatively unsaturated reactive metal centers. The coordinatively unsaturated metal centers can also bind CO through the nucleophilic carbonyl carbon, and at this point a series of reversible insertions can be postulated to account for the observed oxygen scrambling. One skilled in the art may be able to use knowledge of these mechanisms and optimize the process for $CO_2$ utilization via conversion to CO accordingly.

6.4. Tin/Iron Oxide Larger Scale Demonstration

Demonstration of Production of Carbon Monoxide from Carbon Dioxide and a Solid Carbon Source A bench-scale fluidized bed reactor was used to demonstrate the formation of CO using $CO_2$, a solid carbon source, and a promoted catalyst. The fluidized bed reactor consists of a ¾ inch in diameter stainless steel pipe 5 inches long with a disengagement zone that expands to 1.5 inches in diameter. A stainless steel frit is used to hold up the catalyst bed and solid carbon source particles. In this study, $SnO_2Al_2O_3(Fe_2O_3)_3$ promoted with K and Mg was used as the catalyst and pet coke char was used as the solid carbon source. The pet coke was treated at 800° C. for 6 hours in a nitrogen purge to produce the pet coke char. Catalyst and pet coke char particles were mixed together and loaded into the reactor. The reactor is heated to reaction temperature, typically 800° C., in a nitrogen purge. The reaction is initiated by directing a $CO_2$ stream to the fluidized bed and product gases are measured using a $CO/CO_2$ analyzer. The product stream from the reactor is diluted with a 200 sccm nitrogen stream before the analyzer to maintain the minimum flow required for the analyzer.

Elementary reaction experiments were also performed much like in the TGA to observe each step in the proposed mechanism on a larger scale. In each of these experiment steps, the catalyst (and solid carbon source in the fourth step) was heated in the gas specified in Table 3. The first step is a temperature ramp to 800° C. in $N_2$ to desorb any gas species from the surface of the catalyst. Step 2 is a temperature ramp to 800° C. in 10% CO to reduce the catalyst as proposed in the mechanism. Step 3 is a temperature ramp to 800° C. in pure $CO_2$ to observe if the catalyst can be oxidized by the $CO_2$ to form CO. Step 4 is a temperature ramp to 800° C. with the presence of pet coke char in $N_2$ to observe CO formation using the oxygen stripped from the $CO_2$ and the carbon in the pet coke char to form CO. Table 3 shows the conditions for each elementary reaction step.

TABLE 3

Reaction conditions for each step in the fluidized-bed reactor

| Step | Temperature ramp rate (° C./min) | Hold Temp. (° C.) | Gas | Flow rate (SCCM) | $N_2$ Product Dilution (SCCM) |
| --- | --- | --- | --- | --- | --- |
| 1 | 10 | 800 | $N_2$ | 100 | 200 |
| 2 | 10 | 800 | 10% CO in $N_2$ | 100 | 200 |
| 3 | 10 | 800 | $CO_2$ | 100 | 200 |
| 4* | 10 | 800 | $N_2$ | 100 | 200 |

*Note: Pet coke char was added to the catalyst before Step 4

Bench-Scale Fluidized Bed Reactor Results

The following results describe the observations seen from the elementary step reactions performed in the fluidized bed reactor outlined in Table 3. It is important to note that the CO and $CO_2$ vol % profiles shown in the Figures below include a 200 SCCM (~66% of total flow rate) dilution stream required by the analyzer.

FIG. 11 shows the temperature, CO, and $CO_2$ profiles during the temperature ramp, hold, and cool-down of elementary reaction step 1 in $N_2$. CO and $CO_2$ begin to desorb from the surface of the catalyst during the temperature ramp and their concentrations in the gas phase begin to peak near the hold temperature of 800° C.

FIG. 12 shows the CO and $CO_2$ profiles as a function of temperature. During the temperature ramp, $CO_2$ begins to desorb around 400° C. and reaches a peak of 0.2 vol % at 750° C. Then, the $CO_2$ concentration drops off near 0 vol % in the first 20 minutes of the hold time. CO is also observed desorbing in the 700 to 800° C. range, but at very low levels in the ppm range. These observations confirm the $CO_2$ and CO desorption seen in the TGA experiments. They differ somewhat in the specific temperature at which they are observed compared to TGA and MS results. This could be due to the presence of potassium and magnesium promoters on the surface of the catalyst materials used in the fluidized bed reactor, which could cause $CO_2$ to be absorbed as carbonates.

FIG. 13 shows the temperature, CO, and $CO_2$ profiles during the temperature ramp and hold of elementary reaction step 2 in 10% CO with the remaining balance $N_2$. The CO concentration begins to decrease while $CO_2$ is produced and begins to increase throughout the temperature ramp indicating that the CO is reducing the catalyst to form $CO_2$. Then, once the hold temperature is reached, the $CO_2$ gradually drops off while CO gradually increases over the next 400 minutes.

FIG. 14 shows the CO and $CO_2$ profiles as a function of temperature. $CO_2$ concentration peaks near 3.5% at 750° C. and begins a slow gradual decrease over the next 400 minutes. The amount of $CO_2$ produced is more than expected from just reduction of the catalyst and may indicate that other reactions may be occurring. One possibility is that the forward Bouduard reaction is consuming the CO to form $CO_2$ and C deposits on the surface of the catalyst. Additional evidence could be obtained from MS experiments performed with isotopic CO and $CO_2$ to discern this possibility.

FIG. 15 shows the temperature, CO, and $CO_2$ profiles during the temperature ramp, hold, and cool-down of elementary reaction step 3 in pure $CO_2$. CO is produced during the temperature ramp and begins to decrease near the hold temp of 800° C. About 40 minutes after the temperature hold, the $CO_2$ concentration begins decreasing, as well as the CO, due to a pressure build up before the stainless steel frit holding up the catalyst bed. As a safety measure, the feed gas, $CO_2$, was vented through pressure relief valves and the feed gas flow rate to the catalyst bed was greatly reduced resulting in the $CO_2$ concentration dropping off. However, it is still observed that $CO_2$ was consumed and CO produced indicating that the catalyst was being oxidized by the $CO_2$ to form CO.

FIG. 16 shows the CO and $CO_2$ profiles as a function of temperature. CO is produced near 400° C. and increases to a peak of 15% near 700° C. and begins decreasing for the next 40 minutes of the hold section.

FIG. 17 shows the temperature, CO, and $CO_2$ profiles during the temperature ramp, hold, and cool-down of elementary reaction step 4 in $N_2$. Pet coke char was added to the catalyst bed at ambient temperature before the ramp while maintaining an $N_2$ purge to prevent air from entering the reactor and contacting the catalyst. CO and $CO_2$ are produced in a short amount of time near the end of the temperature ramp section.

FIG. 18 shows the CO and $CO_2$ profiles as a function of temperature. $CO_2$ was observed at low levels from 200 to 600° C. during the temperature ramp and began to sharply increase to a peak of 1.7% near 800° C. before quickly dropping off to low levels 30 min after reaching 800° C. CO was also produced and followed a similar profile peaking just above 0.5%. The observation of CO shows the formation of C—O bonds between pet coke and oxygenated catalyst while the observation of a high percentage of $CO_2$ indicates that scrambling mechanisms are definitely occurring on the same time scale as the CO dissociation. Further, it may indicate that the rate limiting step to the mechanism could be dissociation of CO from the active site of the catalyst. In a $CO_2$ dilute environment the rate of CO dissociation from the active site should be slower if the rate law is directly dependent on the concentration of $CO_2$ (needed to displace CO from the site and reoxidize the catalyst).

It is also noteworthy that the amount of $CO_2$ observed during this step is somewhat high and unexpected between ~200-600° C. It is possible that some $CO_2$ from step 3 may have adsorbed without conversion to CO in step 3. Then, in a $CO_2$ dilute environment the $CO_2$ could desorb. However, if it were truly simple physical adsorption, all $CO_2$ would be anticipated to be purged away well before the temperature reaches 200° C. The observation of approximately 0.25 vol % $CO_2$ above 200° C. could be explained by any of several reactions of the various oxides with carbon to produce $CO_2$. For example, $SnO_2$ is thermodynamically favored to be reduced by carbon to make carbon monoxide and is likely also be favorable for $CO_2$ formation. The increase observed near 800° C. is in firm agreement with thermodynamic calculations and is likely the involvement of sites which are harder to reduce. Very little CO was produced in step 4 relative to $CO_2$, again consistent with explanations involving a reduced rate of CO displacement and more extensive oxidation of pet coke.

6.5. Ruthenium/Iron Oxide Carbon Dioxide Utilization

Dry hydrocarbon reforming is the process of converting $C_xH_{2x+2}$ and $CO_2$ to syngas containing CO and $H_2$, typically including some $H_2O$ and $CO_2$. The conversion approaches 100% near 800° C.

A few pivotal papers for the field were published in the early 1990's by Ashcroft et al.[1] and researchers from Haldor Topsoe.[2]. The HaldorTopsoe work included numerous transition metals on MgO support, one being Ru.[2] Several researchers have investigated ruthenium-based systems for dry methane reforming since. In 1999, Matsui et al. investigated 5 wt % Ru on $La_2O_3$, $Y_2O_3$, $ZrO_2$ and $Al_2O_3$ at 600° C. and approximately 1 atm $CO_2$ and $CH_4$ pressures finding that $CO_2$ and methane are readily converted to synthesis gas on $La_2O_3$, $Y_2O_3$, and $Al_2O_3$ supports.[3]. Near that time Bradford et al. reported ruthenium (0.5-5%) on $Al_2O_3$, $TiO_2$, and carbon and tested low pressure streams (0.225 $CO_2$, 0.225 $CH_4$, 0.55 He) observing 11-12% $CO_2$ conversions at 450° C.[4] Crisafulli et al. took the approach of impregnating nickel catalysts with ruthenium to improve the performance for dry methane reforming. [5] Nickel (~2%) supported on $SiO_2$ and H-ZSM5 was impregnated with Ru (0.1-0.6%) and showed reforming of methane (0.15 atm $CH_4$, 0.15 atm $CO_2$) at 600° C. to improve with increasing Ru concentration. A perovskite formulation was studied, $CaRuO_3$ [6] as well as a mixed-metal perovskites of lanthanides (La, Sm, Nd) with Ru—Ni co-catalysts ($Ln_{1-x}Ca_xRu_{0.8}Ni_{0.2}O_3$)[7]. The perovskites showed high conversion of $CH_4$ and $CO_2$ to CO at 700° C. and 800° C. at 1 atm total pressure. Ruthenium was investigated on $Al_2O_3$ and $SiO_2$ at 1 wt % loadings[8], where in a dilute gas mixture (0.1 atm $CH_4$, 0.1 atm $CO_2$, 0.8 atm helium) at 550° C., the methane conversions are 12-14% increased to 52-57% at 750° C. Sutton et al. also probed 1 wt % Ru on $Al_2O_3$ for dry methane reforming applied to biomass gasification.[9] More recently, Haldor Topsoe has reported on Ru supported on $ZrO_2$ at low pressures (~0.21 bar $CH_4$: 0.83 bar $CO_2$, 1.3 bar total pressure)[10] while others have reported on a combined partial methane oxidation/carbon dioxide reforming application at low temperature (550° C.) with 8 wt % ruthenium on $Al_2O_3$ doped with cerium.[11]

To our knowledge, no one has reported co-catalyst formulations of ruthenium and iron for dry hydrocarbon reforming or dry methane reforming or for the application of the catalyzed dry reforming reaction to any synthesis gas process, such as integrated gasification combined cycle (IGCC), biomass gasification, or Fischer-Tropsch synthesis of liquid transportation fuels. Ru—Zr—Fe metal alloys (approximately equal percentages of each metal) have been reported for the methanation of $CO_2$ at 100° C. using $H_2$ (hydrogenation) but not for syngas via dry methane reforming.[12]

We recently discovered that mixed metal oxides of iron and small amounts of ruthenium (~0.5-1.5 wt %) can be formulated by standard co-precipitation methods, and that mixed metal oxides thereof catalyze the dry reforming of methane utilizing $CO_2$ as the oxygen source (dry methane reforming) Mechanistic investigation indicates that oxygen spillover occurs, whereby in separate steps, we observe that the fully-reduced catalyst begins to react with pure $CO_2$ at approximately 400° C., increasing in mass until the weight equals the weight of the oxidized Ru—Fe starting material. Exposure of this oxidized catalyst to pure methane shows weight loss of similar magnitude with concomitant production of CO and $H_2$ (FIGS. 19-20). The onset of this reactivity is between 500 and 600° C. with apex in activity at 600° C. This activity has been observed in separate reaction steps with the aid of thermogravimetric analysis and mass spectroscopy, shown below. Reduction with CO results in a 22% weight loss which looks fully reversible when oxidized with $CO_2$. The magnitude is indicative of oxygen spillover between Fe and Ru since Ru is present in only a small, catalytic, amount relative to $Fe_2O_3$. When the reoxidized catalyst was purged with $CH_4$, it again showed a significant weight loss, even higher than the weight loss observed during reduction with CO. Even more promising, the predominant products as indicated by MS are CO and $H_2$, with only a small amount of $CO_2$ detected. Under these conditions, this catalyst appears promising for further development.

We have also observed that the material is active in a fixed-bed reactor system under a co-feed of $CO_2$ and $CH_4$ and confirmed the formation of CO and $H_2$. Results are provided below (FIGS. 21-24). Highlights are that at approximately 600° C. and 25 bar of a feed mixture ($CH_4$:$CO_2$=6:1), we observed production of approximately 10 vol % CO and 10 vol % hydrogen. In terms of $CO_2$ conversion we observed approximately 30% conversion. When the total pressure is reduced to approximately 1 bar, the $CO_2$ conversion is approximately 16%. When the feed composition is changed to a $CO_2$:$CH_4$ ratio of 1:1 and 1 bar total pressure, approximately 2 vol % CO is formed (~3% $CO_2$ conversion) at 500° C., whereas at 600° C., approximately 5 vol % CO and 1 vol % $H_2$ are made (approximately 12% $CO_2$ conversion). When the temperature is raised to 800 C approximately 30 volume percent CO is formed and 10 volume percent hydrogen. See FIG. 24 showing the performance of the Ru—Fe catalyst at 630° C. and 780° C. with a total of 1 atm natural gas and carbon dioxide mixture (1 mol $CH_4$: 1 mol $CO_2$). In all cases when the total pressure is increased to 50 bar, no synthesis gas products are observed.

At this point the $CO_2$-methane reforming catalyst formulation could be incorporated into a process by modifying the catalyst formulation to include an additional phase capable of forming a target product from the synthesis gas made by the Ru—Fe phase. Such products are methanol or Fischer-Tropsch fuels. For methanol synthesis, the approach would be to develop a catalyst with a copper component similar to the copper-zinc aluminate catalyst used for commercial methanol synthesis. The copper-zinc aluminate could be incorporated as an additional phase to the current dry methane reforming formulation, with the goal being to run the process in a single reactor using a single bifunctional catalyst material. However, it does not necessarily have to be done this way, and in fact, since the process conditions which we have currently observed for our dry methane reforming catalyst are lower in pressure and higher in temperature than the conditions currently encountered in methanol synthesis from syngas, the accomplishment may be difficult to achieve. To avoid this difficulty, we could set the process up in two reaction zones, with the synthesis gas produced from $CO_2$ and $CH_4$ being fed to a methanol synthesis zone. The dry methane reforming catalyst and the methanol synthesis catalyst would be kept separate.

Fischer-Tropsch fuels from $CO_2$-derived synthesis gas is another process which could incorporate the new Ru—Fe catalyst. Like the methanol approach, the objective is conversion of the syngas to liquid fuels, but in this case it makes a little more sense to consider a single catalyst approach. The current formulation contains components which are known to have FT-activity and we currently know that synthesis gas can be produced at pressures which could be used in high-temperature FT processes. In one embodiment, the temperature of the $CO_2$-derived synthesis gas is lowered by few hundred degrees, while moving the synthesis gas from the $CO_2$-utilization zone to the FT-zone, where it will be converted to transportation fuels.

The ruthenium-iron mixed metal oxide can be prepared by the following preparation. For the preparation of approximately 2.00 g $Ru_{0.01}$ $FeO_{1.52}$, 2.00 g of ruthenium nitrosyl nitrate (Strem Chemicals, 1.5% Ru) and 10.01 g of iron (III) nitrate nonahydrate (Sigma Aldrich, ≥98%) were dissolved into 100.70 g of deionized water. The pH of the solution was 1.23. 34.55 g of 9.07 wt % NaOH solution was added drop-wise while mixing on a stir plate to reach pH 7.56. The solids were collected via vacuum filtration and then washed with 1 L of deionized water. The pH of the final 25 mL of wash filtrate was ~6.5 by pH strip. The wet cake, 12.61 g, was dried overnight at 120° C. and then calcined at 650° C. for 2 hours after a ramp up at 3° C./min A total of 1.93 g was collected, a 95.5% yield. Elemental analysis by ICP-MS showed Ru 1.2%, Fe 71.9%, theory Ru 1.2%, Fe 68.8%.

6.6. References for Section 6.5 (Ruthenium Oxide Iron Oxide)

1. Ashcroft, A. T.; Cheetham, A. K.; Green, M. L. H.; Vernon, P. D. F., PARTIAL OXIDATION OF METHANE TO SYNTHESIS GAS-USING CARBON-DIOXIDE. Nature 1991, 352, (6332), 225-226.
2. Rostrup-Nielsen, J. R.; Hansen, J.-H. B., Journal of Catalysis 1993, 144, 38.
3. Matsui, N.; Anzai, K.; Akamatsu, N.; Nakagawa, K.; Ikenaga, N.; Suzuki, T., Reaction mechanisms of carbon dioxide reforming of methane with Ru-loaded lanthanum oxide catalyst. Applied Catalysis a-General 1999, 179, (1-2), 247-256.
4. Bradford, M. C. J.; Vannice, M. A., CO2 reforming of CH4 over supported Ru catalysts. Journal of Catalysis 1999, 183, (1), 69-75.
5. Crisafulli, C.; Scire, S.; Minico, S.; Solarino, L., Ni—Ru bimetallic catalysts for the CO2 reforming of methane. Applied Catalysis a-General 2002, 225, (1-2), 1-9.
6. Reller, A.; Davoodabady, G.; Portmann, A.; Oswald, H. R. In The 8th European COngress on Electron Microscopy, Budapest, 1984; Budapest, 1984.
7. Goldwasser, M. R.; Rivas, M. E.; Pietri, E.; Perez-Zurita, M. J.; Cubeiro, M. L.; Gingembre, L.; Leclercq, L.; Leclercq, G., Perovskites as catalysts precursors: CO2 reforming of CH4 on Ln(1-x)Ca(x)Ru(0.8)Ni(0.2)O(3) (Ln=La, Sm, Nd). Applied Catalysis a-General 2003, 255, (1), 45-57.
8. Ferreira-Aparicio, P.; Rodriguez-Ramos, I.; Anderson, J. A.; Guerrero-Ruiz, A., Mechanistic aspects of the dry reforming of methane over ruthenium catalysts. Applied Catalysis a-General 2000, 202, (2), 183-196.
9. Sutton, D.; Parle, S. M.; Ross, J. R. H., The CO2 reforming of the hydrocarbons present in a model gas stream over selected catalysts. Fuel Processing Technology 2002, 75, (1), 45-53.
10. Jakobsen, J. G.; Jorgensen, T. L.; Chorkendorff, I.; Sehested, J., Steam and CO2 reforming of methane over a Ru/ZrO2 catalyst. Applied Catalysis a-General 2010, 377, (1-2), 158-166.
11. Ji, H.; Feng, D.; He, Y., Low-temperature utilization of CO2 and CH4 by combining partial oxidation with reforming of methane over Ru-based catalysts. Journal of Natural Gas Chemistry 2010, 19, (6), 575-582.
12. Tada, T.; Habazaki, H.; Akiyama, E.; Kawashima, A.; Asami, K.; Hashimoto, K., AMORPHOUS FE-VALVE METAL-PT GROUP METAL ALLOY CATALYSTS FOR METHANATION OF CO2. Mater. Sci. Eng. A-Struct. Mater. Prop. Microstruct. Process. 1994, 182, 1133-1136.

It is to be understood that, while the invention has been described in conjunction with the detailed description, thereof, the foregoing description is intended to illustrate and not limit the scope of the invention. Other aspects, advantages, and modifications of the invention are within the scope of the claims set forth below. All publications, patents, and patent applications cited in this specification are herein incorporated by reference as if each individual publication or patent application was specifically and individually indicated to be incorporated by reference.

What is claimed is:

1. A method for converting a hydrocarbon to an oxygenated hydrocarbon which comprises contacting a mixed transition iron (II/III) metal catalyst for catalyzing $CO_2$ oxidation of the hydrocarbon, wherein the mixed transition metal iron (II/III) catalyst is an iron (II/III) and a second metal oxide selected from the group consisting of Ag, Bi, Co, Cu, La, Mn, Sn, Ru, and Zn, and an appropriate $CO_2$ feed stream under appropriate conditions so as to form the oxygenated hydrocarbon.

2. The method of claim 1, wherein the hydrocarbon is an alkane, an alkene, an alkyne, an aromatic compound, a cyclic compound, a polyaromatic compound or a polycyclic compound.

3. The method of claim 2, wherein the alkane is butane, ethane, methane, or propane.

4. The method of claim 2, wherein the alkene is ethylene or propylene.

5. The method of claim 1, wherein the oxygenated hydrocarbon is an alcohol, aldehyde, an anhydride, a carboxylic acid, an ester, an ether, an epoxide, or a ketone.

6. The method of claim 5, wherein the epoxide is ethylene oxide or propylene oxide.

* * * * *